(12) United States Patent
Schindler et al.

(10) Patent No.: US 7,704,740 B2
(45) Date of Patent: Apr. 27, 2010

(54) NANOFIBRILLAR STRUCTURE AND APPLICATIONS INCLUDING CELL AND TISSUE CULTURE

(75) Inventors: Melvin S. Schindler, Piscataway, NJ (US); Hoo Young Chung, Bloomington, MN (US)

(73) Assignee: Michigan State University, East Lansing, MI (US)

( * ) Notice: Subject to any disclaimer, the term of this patent is extended or adjusted under 35 U.S.C. 154(b) by 1022 days.

(21) Appl. No.: 10/703,169

(22) Filed: Nov. 5, 2003

(65) Prior Publication Data

US 2005/0095695 A1 May 5, 2005

(51) Int. Cl.
C12N 5/00 (2006.01)
(52) U.S. Cl. ..................... 435/398; 435/395
(58) Field of Classification Search ......... 435/375–377, 435/373, 395, 399, 400, 283.1, 289.1, 398, 435/325
See application file for complete search history.

(56) References Cited

U.S. PATENT DOCUMENTS

| | | | |
|---|---|---|---|
| 5,672,399 A | 9/1997 | Kahlbaugh et al. | 428/36.1 |
| 6,146,892 A * | 11/2000 | Ma et al. | 435/399 |
| 6,787,357 B2 * | 9/2004 | Bowlin et al. | 435/395 |
| 2002/0042128 A1 | 4/2002 | Bowlin et al. | 435/366 |
| 2002/0081732 A1 | 6/2002 | Bowlin et al. | 435/446 |
| 2002/0090725 A1 | 7/2002 | Simpson et al. | 435/402 |
| 2002/0094514 A1 | 7/2002 | Bowlin et al. | 435/2 |
| 2002/0133229 A1 | 9/2002 | Laurencin et al. | 623/13.17 |
| 2002/0173213 A1 | 11/2002 | Chu et al. | 442/414 |
| 2002/0192468 A1 | 12/2002 | Choi et al. | 428/392 |
| 2003/0017208 A1 | 1/2003 | Ignatious et al. | 424/486 |
| 2003/0050711 A1 | 3/2003 | Laurencin et al. | |
| 2003/0054035 A1 | 3/2003 | Chu et al. | 424/486 |
| 2003/0211130 A1 | 11/2003 | Sanders et al. | 424/423 |
| 2003/0215624 A1 | 11/2003 | Layman et al. | 428/221 |
| 2004/0037813 A1 * | 2/2004 | Simpson et al. | 424/93.7 |

FOREIGN PATENT DOCUMENTS

| | | |
|---|---|---|
| WO | WO 02/062961 A2 | 8/2002 |
| WO | WO 03/024297 | 3/2003 |
| WO | WO 03/072748 | 9/2003 |
| WO | WO 03/084980 A2 | 10/2003 |
| WO | WO 03/086290 | 10/2003 |
| WO | WO 2004/018628 A2 | 3/2004 |

OTHER PUBLICATIONS

Abrams, G.A., et al., "Nanoscale topography of the basement membrane underlying the corneal epithelium of the Rhesus Macaque," *Cell Tissue Res*, 2000, 299:39-46.
Bhadriraju et al., "Engineering cellular microenvironments to improve cell-based drug testing," *Drug Discovery Today*, Jun. 2002, 7(11):612-620.
Boudreau, N.J., "Organized living: from cell surfaces to basement membranes," *Sci STKE*, 2003, 2003(196):pe34.
Cukierman et al., "Cell interactions with three-dimensional matrices," *Curr. Opin. Cell Biol*, 2002, 14(5):633-9.
Grinnell, F., "Fibroblast biology in three-dimensional collagen matrices," *Trends Cell Biol.*, 2003, 13(5):264-9.
Katz et al., "Physical state of the extracellular matrix regulates the structure and molecular composition of cell-matrix adhesions," *Mol. Biol. Cell*, 2000, 11(3):1047-60.
Kisiday et al., "Self-assembling peptide hydrogel fosters chondrocyte extracellular matrix production and cell division: implications for cartilage tissue repair," *Proc. Natl. Acad. Sci. USA*, 2002, 99(15):9996-10001.
Levenberg et al., "Differentiation of human embryonic stem cells on three-dimensional polymer scaffolds," *Proc. Natl. Acd. Sci. USA*, 2003, 100(22):12741-6.
Lutolf et al., "Synthetic matrix metallo-proteinase-sensitive hydrogels for the conduction of tissue regeneration: Engineering: cell-invasion characteristics," *Proc. Natl. Acad. Sci. USA*, 2003, 100(9):5413-5418.
Matthews, J., et al., "Electrospinning of Collagen Nanofibers," *Biomacromolecules*, 2002, 3:232-238.
Pelham et al., "Cell locomotion and focal adhesion are regulated by substrate flexibility," *Proc. Natl. Acad. Sci. USA*, 1997, 94:13661-13665.
Petersen, O.W., et al., "Interaction with basement membrane serves to rapidly distinguish growth and differentiation pattern of normal and malignant human breast epithelial cells," *Proc. Natl. Acad. Sci. USA*, 1992, 89(19):9064-8.
Schmeichel, K.L., et al., "Modeling tissue-specific signaling and organ function in three dimensions," *J. Cell Sci.*, 2003, 116(Pt 12):2377-88.

(Continued)

*Primary Examiner*—Irene Marx
*Assistant Examiner*—Susan Hanley
(74) *Attorney, Agent, or Firm*—Merchant & Gould P.C.

(57) ABSTRACT

A nanofibrillar structure for cell culture and tissue engineering is disclosed. The nanofibrillar structure can be used in a variety of applications including methods for proliferating and/or differentiating cells and manufacturing a tissue. Also disclosed is an improved nanofiber comprising a lipid, lipophilic molecule, or chemically modified surface. The nanofibers can be used in a variety of applications including the formation of nanofibrillar structures for cell culture and tissue engineering.

60 Claims, 6 Drawing Sheets

OTHER PUBLICATIONS

Wang et al., "Reciprocal interactions between beta 1-integrin and epidermal growth factor receptor in three-dimensional basement membrane breast cultures: a different perspective in epithelial biology," *Proc. Natl. Acad. Sci. USA*, 1998, 95(25):14821-6.

Wozniak et al., "Rock-generated contractility regulates breast epithelial cell differentiation in response to the physical properties of a three-dimensional collagen matrix," *J. Cell Biol.*, 2003, 163(3):583-95.

Yamada et al., "Cell biology: survival in three dimensions," *Nature*, 2002, 419(6909):790-1.

Yamada et al., "Dimensions and dynamics in integrin function," *Brazilian J. of Medical and Biol. Res.*, 2003, 36:959-966.

Yoshimoto et al., "A biodegradable nanofiber scaffold by electrospinning and its potential for bone tissue engineering," *Biomaterials*, May 2003, 24(12):2077-82.

Fertala, A. et al., "Mapping critical sites in collagen II for rational design of gene-engineered proteins for cell-supporting materials," *J. Biomed. Mater. Res.*, vol. 57, pp. 48-58 (2001).

Li, W. et al., "Electrospun nanofibrous structure: A novel scaffold for tissue engineering," *J. Biomed. Mater. Res.* vol. 60, pp. 613-621 (2002).

Mo, X. et al., "Electrospun P(LLA-CL) nanofiber: a biomimetic extracellular matrix for smooth muscle cell and endothelial cell proliferation," *Biomaterials*, vol. 25, pp. 1883-1890 (2004).

Zhang, S., "Fabrication of novel biomaterials through molecular self-assembly," *Nature Biotechnology*, vol. 21, No. 10, pp. 1171-1178 (Oct. 2003).

*Engineering Research News, National University Singapore*, Feb. 2003, vol. I8 "Textile and Nanofibrous Scaffolds for Tissue Engineering."

Abbott, A., 2003, *Nature*, 424:870-872 "Biology's new dimension."

Bowlin, G., 2004 (May), *Materials Today*, 7:64 "A new spin on scaffolds."

Jin et al., 2004, *Biomaterials*, 25:1039-1047 "Human bone marrow stromal cell responses on electrospun silk fibroin mats."

Ko et al., 1998, *24th Annual Meeting of the Society for Biomaterials*, Apr. 22-26, 1998, San Diego, CA, p. 11 "The Dynamics of Cell-Fiber Architecture Interaction."

Silva et al., 2004, *Science*, 303:1352-1355 "Selective Differentiation of Neural Progenitor Cells by High-Epitope Density Nanofibers."

Abbott et al., "Biology's new dimension," 2003, *Nature*, 424:870-872.

Bottaro et al., 2002, *Ann. N. Y. Acad. Sci.*, 961:143-153.

Chiu et al., 2000, *Proc. Natl. Acad. Sci. USA*, 97:2408-2413.

Cukierman et al., 2001, *Science*, 294:1708-1712.

Grinnell et al., 2003, *Mol. Biol. Cell*, 14:384-395.

Jacks and Weinberg, 2002, *Cell*, 111:923-925.

Kunz-Schughart et al., 2003, *Am. J. Physiol. Cell Physiol.*, 284:C209-C219.

Li et al., 2003, *FASEB J.*, 17:97-99.

Mueller-Klieser, 1997, *Am. J. Physiol.*, 273:C1109-C1123.

Padron et al., 2000, *Crit. Rev. Oncol./Hematol.*, 36:141-157.

Tamariz and Grinnell, 2002, *Mol. Biol. Cell*, 13:3915-3929.

Walpita and Hay, 2002, *Nature Rev. Mol. Cell. Biol.*, 3:137-141.

Weaver et al., 2002, *Cancer Cell*, 2:205-216.

Candiello et al., 2007, *Biochemical properties of native basement membranes*. FEBS Journal, 274:2897-2908.

Le Bleu et al., 2007, *Structure and Function of Basement Membranes*. Exp. Biol. Med., 232:1121-1129.

Search Report and Written Opinion mailed Jan. 21, 2009.

\* cited by examiner

4A

4B

4C

5A

5B

NANOFIBRILLAR STRUCTURE AND APPLICATIONS INCLUDING CELL AND TISSUE CULTURE

FIELD OF THE INVENTION

The invention relates to a nanofibrillar structure for cell culture and tissue engineering and methods for proliferating and/or differentiating cells and manufacturing a tissue. Another aspect of the invention relates to a growth media for cell culture comprising a matrix of nanofibers. Another aspect of the invention relates to an improved nanofiber comprising a lipid, lipophilic molecule, or chemically modified surface. The improved nanofiber is useful in a variety of applications. In one application, a nanofibrillar structure for cell culture and tissue engineering may be prepared using the improved nanofiber. In another application, a media for cell culture may be prepared using the improved nanofiber.

BACKGROUND OF THE INVENTION

Cell proliferation and differentiation in vivo is regulated by unique spatial interactions between cells. Spatial cues in conjunction with the topologically distinct location of specific attachment molecules, and the release of specific humoral factors, such as growth and differentiation factors, function as signals to the cell to proliferate, differentiate, migrate, remain in a resting state, or initiate apoptosis. The capacity of the cell to respond to these signaling triggers is dependent on the availability of specific cell surface and intracellular receptors. The signal transduction pathways that are stimulated by these molecules depend on the organization and structure of the cell cytoskeleton whose architecture is a function of multipoint cell surface interactions with these signaling molecules, surrounding cells, and extracellular matrix.

In designing cell and tissue culture environments, it is important to consider the cellular interactions that must be incorporated into the growth environment. Cell types, spatial cues, and chemical triggers and modulators play a significant role in regulating gene expression within interacting cells (Li et al., 2002, *FASEB J.*, 17:97-99; Botarro et al., 2002, *Ann. N.Y. Acad. Sci.*, 961:143-153; Kunz-Schughart et al., 2003, *Am. J. Physiol. Cell Physiol.*, 284:C209-C219; Cukierman et al., 2001, *Science*, 294:1708-1712). Past advances in the practice of cell and tissue culture have been directed toward providing the biochemical and physical conditions that approximate the complex in vivo microenvironment within a tissue (Cukierman et al., 2001, *Science*, 23:1708-1712; Li et al., 2002, *FASEB J.*, 17:97-99; Chiu et al., 2000, *Proc. Natl. Acad. Sci. USA*, 97:2408-2413). These efforts have been limited by factors that include the use of cell lines that have been continuously grown on and selected for their ability to proliferate on planar culture surfaces that lack the spatial cues and chemical triggers and modulators present in tissue in vivo.

Recent work has demonstrated that the unique micro- and nano-environments resulting from spatial organization of nanofibrils in three dimensions, such as collagen and other fibrillar elements of the extracellular matrix, is essential for tissue-like patterns of cell adherence, signal transduction, and differentiated function. The attachment and growth of cells on solid planar culture surfaces elicits a different pattern of cellular organization from that observed for cells in tissues in vivo (Walpita and Hay, 2002, *Nature Rev. Mol. Cell. Biol.*, 3:137-141; Cukierman et al., 2001, *Science*, 23:1708-1712; Mueller-Klieser, 1997, *Am. J. Physiol.*, C1109-C1123). When grown on a typical planar cell culture surface, fibroblasts, for example, assume a highly spread and adhering morphology in which the actin network located within the cytoplasm is organized into arrays of thick stress fibers. In contrast, when fibroblasts are grown within collagen gels or are observed in tissues, they are spindle-like in shape with actin organized in a cortical ring (Tamariz and Grinnell, 2002, *Mol. Biol. Cell*, 13:3915-3929; Walpita and Hay, 2002, *Nature Rev. Mol. Cell. Biol.*, 3:137-141; Grinnell et al., 2003, *Mol. Biol. Cell*, 14:384-395). Moreover, the drug sensitivity of cancer cells grown in two dimensional cell cultures versus cancer cells grown in three-dimensional cell cultures has been shown to be considerably different; an outcome that has significant bearing on the design of cancer therapies involving chemotherapeutics (Mueller-Klieser, 1997, *Am. J. Physiol.*, 273:C1109-C1123; Padron et al., 2000, *Crit. Rev. Oncol./Hematol.*, 36:141-157; Jacks and Weinberg, 2002, *Cell*, 111: 923-925; Weaver et al., 2002, *Cancer Cell*, 2:205-216).

A significant development in cell culture and tissue culture has been the introduction of matrices composed of non-toxic and biocompatible materials designed to serve as scaffolds and three-dimensional spatial organizers for dividing cells both in vitro and in vivo (U.S. patent application Ser. No. 20020133229; U.S. patent application Ser. No. 20020042128; U.S. patent application Ser. No. 20020094514; U.S. patent application Ser. No. 20020090725). The goal of these designs is to provide a growth surface with in vivo tissue-like geometry and micro- and nano-environments for cells to proliferate and differentiate into functioning tissue or regenerate damaged structures. These structures supporting functional cells can be utilized for a variety of applications, including repairing or replacing damaged tissue in the body and promoting the growth of new tissues and organs.

The successful preparation of three-dimensional cell and tissue culture technology, however, has predominantly been a function of the expertise within individual laboratories and the availability of sophisticated instrumentation. There is a significant need for a culture medium manufactured from simple or composite materials that provides the ease of use, uniformity, quality control, and flexibility associated with the standard tissue culture plate. In addition, the culture medium material and design may allow for the construction of layered assemblies of defined composition that more accurately reflect the organization of cell layers in tissues. A media comprising multiple layers of fine fibers separated by coarse fiber supports, such as the filter media disclosed in U.S. Pat. No. 5,672,399, does not provide an environment for growth of living cells.

SUMMARY OF THE INVENTION

A nanofibrillar structure can be manufactured from a nanofiber material that provides repeatable fiber and matrix dimensions, ease of use, uniformity, cell response, quality control, and flexibility. The nanotopography, the topography of the nanofiber network of the nanofibrillar structure and the arrangement of the nanofibers of the nanofiber network in space is engineered to provide an in vitro biomimetic substratum that is more tissue-compatible for the promotion of homotypic or heterotypic cell growth and/or cell differentiation in single layer or multi-layered cell culture.

One aspect of the invention provides an improved nanofiber comprising a lipid. The nanofiber has a diameter of less than about 1000 nm. The improved nanofiber is useful in a variety of applications, including cell culture and tissue engineering.

A preferred mode of the invention involves a polymeric material combined with an additive composition that influences packing of the polymer such that electrospinning of the polymer results in the production of a polydisperse plurality of nanofibers having a greater number or percentage of thin fibers as compared to a polydisperse plurality of nanofibers electrospun from a polymer solution not containing the additive composition. In an embodiment, the polymer solution comprises from about 0.25% to about 15% w/w additive composition. In another embodiment, the polymer solution comprises from about 1% to about 10% w/w additive composition. In a preferred embodiment, the additive composition is a lipid. In another preferred embodiment, the lipid is lysophosphatidylcholine, phosphatidylcholine, sphingomyelin, cholesterol, or mixtures thereof. The additive composition may also function as a signaling molecule inducing recruitment and attachment of cells to the fiber.

Thin fibers preferably have a diameter of about 5 nm to about 600 nm. In an embodiment, thin fibers have a diameter of about 50 nm to about 400 nm. In another embodiment, thin fibers have a diameter of about 300 nm. In another embodiment, thin fibers have a diameter of about 5 nm to about 200 nm. In another embodiment, thin fibers have a diameter of about 5 nm to about 100 nm. In another embodiment, thin fibers have a diameter of about 5 nm to about 50 nm.

Nanofibers having a smaller diameter provide a surface that promotes multiple point attachments between nanofibers and cells, a characteristic of cell attachment to the extracellular matrix in vivo. Preferably at least about 25% of the polydisperse plurality of nanofibers is thin fibers. In an embodiment, at least about 30% percent of the polydisperse plurality of lipid containing nanofibers are thin fibers. In another embodiment, at least about 40% of the polydisperse plurality of lipid containing nanofibers is thin fibers. In another embodiment, at least about 50% of polydisperse plurality of lipid containing nanofibers is thin fibers. In another embodiment, at least about 60% of polydisperse plurality of lipid containing nanofibers is thin fibers. In another embodiment, at least about 70% of polydisperse plurality of lipid containing nanofibers is thin fibers.

In an embodiment, the improved nanofibers are fabricated from a polyamide, polyester or other polymer suitable for in vivo, animal or human application. In another embodiment, the polyester may be poly($\epsilon$-caprolactone), poly(lactate), or poly(glycolate). In another embodiment, the nanofibers are fabricated from a polymer solution comprising at least about 10% poly($\epsilon$-caprolactone) w/w in chloroform. In another embodiment, the nanofibers are fabricated from a polymer solution comprising at least about 15% poly($\epsilon$-caprolactone) w/w in chloroform.

Another preferred mode of the invention involves a nanofiber comprising one or more bioactive molecules including, but not limited to peptide, polypeptides, lipids, carbohydrates, polysaccharides, amino acids, nucleotides, nucleic acids, polynucleotides, or hybrid mixtures thereof. Polypeptides include fibrous proteins, adhesion proteins, growth factors, and differentiation factors. Some preferred growth factors include VEGF, NGFs, PDGF-AA, PDGF-BB, PDGF-AB, FGFb, FGFa, and BGF. Some preferred differentiation factors include neurotrophins, colony stimulating factors, and transforming growth factors.

In one embodiment, the bioactive molecule is incorporated into the polymer solution from which the nanofiber is fabricated. In another embodiment, functional groups may be attached to an outside surface of the nanofiber and the functionalized surfaces of the nanofiber reacted to bind one or more bioactive molecules. In one embodiment, functional groups are attached to an outside surface of the nanofiber using plasma deposition. In another embodiment, functional groups are incorporated into the polymer solution from which the nanofiber is fabricated.

Another preferred mode of the invention involves a nanofiber comprising a fluorescent marker. The fluorescent marker allows, for example, visualization of a nanofiber, identification of specific nanofibers within a nanofiber blend, identification of a chemical or physical property of a nanofiber or the nano-environment surrounding the nanofiber, and evaluation of the degradation of and/or redistribution of implantable nanofibers and/or structures comprising nanofibers, including three-dimensional structures useful for engineering tissue.

The fluorescent marker may comprise an organic dye fluorophore. In an embodiment, the fluorophore is added to the polymer prior to electrospinning of a nanofiber. In another embodiment, the fluorophore is conjugated to a nanofiber via a functional group incorporated at the surface of the nanofiber. In another embodiment, the fluorophore is conjugated to a bioactive molecule that is attached to a nanofiber. The fluorescent marker may comprise colloidal inorganic semiconductor nanocrystals. In an embodiment, the nanocrystals comprise a CdSe core and ZnS cap. In another embodiment, the nanocrystals comprise quantum dots.

The fluorescent marker may act as an ion-sensing element. In an embodiment, the nanofiber may comprise a fluorescent marker wherein the fluorescence or fluorescent intensity of the marker is dependent upon ion concentration. Such an ion-sensing element is useful to detect changes in ion concentration including pH and calcium, sodium, or phosphate flux. In another embodiment, the fluorescent marker may function as a reporter element to demonstrate complex formation between the nanofiber surface and ligands including, but not limited to, DNA/RNA nucleotide sequences, carbohydrates, or peptides/amino acid sequences. This complex formation can be manifested by changes in fluorescence emission wavelength and/or changes in energy transfer between an absorber and emitter.

The present invention is also directed to a method of identifying a chemical and/or physical property of a nanofiber. In an embodiment, a fluorescent marker is assigned to a chemical or physical property of the nanofiber and the nanofiber is labeled with the assigned fluorescent marker. Such chemical and physical properties include, but are not limited to, fiber diameter, bioactive molecules, functional groups, dissolution or degradation rate of fiber, composition of polymer comprising the nanofiber, hydrophobicity or hydrophilicity of the fiber, solubility of the polymer comprising the nanofiber, toxicity of the polymer, toxicity of bioactive molecules, or combinations thereof. Labeling nanofibers with a specific fluorescent marker, for example, allows for the identification of each type of fiber within a nanofiber blend or cellular array. A nanofiber may be labeled with more than one fluorescent marker in order to identify multiple chemical and/or physical properties of the nanofiber.

Another aspect of the invention is a nanofibrillar structure comprising one or more nanofibers and wherein the nanofibrillar structure is defined by a network of one or more nanofibers. In an embodiment, the nanofiber network is deposited on a surface of a substrate. The nanofiber may be fabricated from a variety of polymers or polymer systems. Preferably the polymer or polymer system is non-cytotoxic. In an embodiment, the nanofibers comprise the improved nanofibers of the invention. In another embodiment, the nanofibers are fabricated from a polyamide or polyester. In a further embodiment, the polyamide or polyester is suitable for in vivo human application. In a further embodiment, the polyester may be poly(ε-caprolactone), poly(lactate) or poly(glycolate). In a further embodiment, the polyamide may be a nylon 6, a nylon 66, a nylon 610 or other biocompatible polyamides. In an embodiment, the film is an optically clear polyester film.

In an embodiment, the substrate comprises glass or plastic. In a further embodiment, the substrate is a surface of a culture container. In another embodiment, the substrate comprises a film. The film may be water soluble or water insoluble. The film may be biodegradable and/or biodissolvable. Preferably the film is non-cytotoxic. In a preferred embodiment, the film is polyvinyl alcohol film.

The nanofibrillar structures may be utilized singly or layered to form a multi-layered assembly of nanofibrillar structures for cell or tissue culture. In an embodiment, the nanofibrillar structure comprises a spacer. The spacer may function as a support structure. The spacer provides sufficient openings to permit cells to penetrate and attach to the nanofiber network. The spacer may be water soluble or water insoluble. The spacer may be porous or non-porous. The spacer may be biodegradable and/or biodissolvable. Preferably the spacer is biocompatible.

In an embodiment, the spacer comprises a first and second surface wherein the first surface of the spacer contacts a surface of the nanofiber network deposited on a substrate and the second surface of the spacer contacts a surface of the substrate such that the nanofiber network and substrate are separated by the diameter or thickness of the spacer. In another embodiment, the spacer comprises a first and second surface wherein the first surface of the spacer contacts a surface of a first nanofibrillar structure and the second surface of the spacer contacts a surface of a second nanofibrillar structure such that the two nanofibrillar structures are separated by the diameter or thickness of the spacer.

The nanofibrillar structure of the invention has many in vivo and ex vivo uses including wound repair, growth of artificial skin, veins, arteries, tendons, ligaments, cartilage, heart valves, organ culture, treatment of burns, and bone grafts. In an embodiment, a diverse array of growth environments for a cell or tissue may be constructed by engineering specific chemical and physical properties into the nanofiber network, substrate, and/or spacers comprising the individual nanofibrillar structure elements and/or sequentially layering individual nanofibrillar structures. In certain embodiments, the unique nature of the environment can be obtained from the heterogeneous nature of the fiber diameter and composition. Physical properties and/or characteristics of the individual nanofiber, nanofibrillar structure, and nanofibrillar network including, but not limited to, texture, rugosity, adhesivity, porosity, solidity, elasticity, geometry, interconnectivity, surface to volume ratio, fiber diameter, fiber solubility/insolubility, hydrophilicity/hydrophobicity, and fibril density may be varied and/or modified to construct nano- and/or micro-environments that promote a desired cellular activity, including proliferation and/or differentiation. Specific nano- and/or micro-environments may be engineered within individual nanofibrillar structures or within a cellular array comprising two or more nanofibrillar structures.

Specific chemical properties and recognition motifs such as polypeptides, lipids, carbohydrates, amino acids, nucleotides, nucleic acids, polynucleotides, or polysaccharides including, but not limited, to growth factors, differentiation factors, fibrous proteins, adhesive proteins, glycoproteins, functional groups, adhesive compounds, deadhesive compounds, and targeting molecules may be engineered into the nanofibrillar network, substrate, and/or spacers of the individual nanofibrillar structures either isotropically or as gradients to promote one ore more selected cellular activities, including growth and/or differentiation. Some preferred growth factors include VEGF, NGFs, PDGF-AA, PDGF-BB, PDGF-AB, FGFb, FGFa, and BGF. Some preferred differentiation factors include neurotrophins, colony stimulating factors, and transforming growth factors. Amino acids, peptides, polypeptides, and proteins may include any type of such molecules of any size and complexity as well as combinations of such molecules including, but are not limited to, structural proteins, enzymes, and peptide hormones.

The present invention is also directed to methods of manufacturing a tissue. In an embodiment, two or more nanofibrillar structures are layered to form a multi-layered nanofibrillar assembly. Viable cells are deposited on the fiber and the structure is cultured under conditions that promote growth, migration and/or differentiation of the deposited cells. In a further embodiment, nano- and/or micro-environments that promote cellular activity may be engineered within an individual matrix by varying and/or modifying selected physical and/or chemical properties of the growth matrix.

In another embodiment, multiple cell types are cultured on individual nanofibrillar structures under different culture conditions. Two or more of the individual nanofibrillar structures are then layered to form a multi-layered nanofibrillar assembly and the assembly is cultured under conditions that promote a desired cellular activity, including growth and/or differentiation of the cells. In a further embodiment, nano- and/or micro-environments that promote cellular activity may be engineered within an individual nanofibrillar structure by varying and/or modifying selected physical and/or chemical properties of the nanofibrillar structure or within the nanofibrillar assembly by selectively layering the individual nanofibrillar structures to obtain the desired nano- or micro-environment. Homogeneous or heterogeneous fiber diameters and compositions may be selected to optimize proliferation and/or differentiation.

Another aspect of the invention is a cell growth media. In an embodiment, the cell growth media comprises a matrix of nanofibers wherein the network has a fiber diameter of about 50 nm to about 1000 nm, an average interfiber spacing of at least about 2 microns, a matrix solidity of about 30 percent, and a top and a bottom with an outerwall wherein the outerwall has a height of about 10 microns to about 100 mm and wherein the top and bottom independently have an area of about 5 $nm^2$ to about $4 \times 10^5$ $mm^2$. In another embodiment, the height of the outerwall and the area of the top and the bottom are adapted to the dimensions of an available culture vessel or container.

The cell growth media may comprise a matrix, network, mat, sheet, or roll. In an embodiment, the cell growth media comprises a network of nanofibers. In another embodiment, the network of nanofibers is adapted for insertion into a culture container. In another embodiment, the cell growth media is deposited onto an inside surface of a culture container.

BRIEF DESCRIPTION OF THE DRAWINGS

FIGS. 1A and B show that nanofibrillar mats composed of randomly deposited polyamide nanofibers can be assembled into layered surfaces. FIG. 1C shows that nanofibers may be electrospun with specific orientation.

DETAILED DESCRIPTION OF THE INVENTION

I. Definitions

Figure 1:
FIGS. 1A-C are scanning electron microscope images of nanofibrillar structures.
Figure 1:
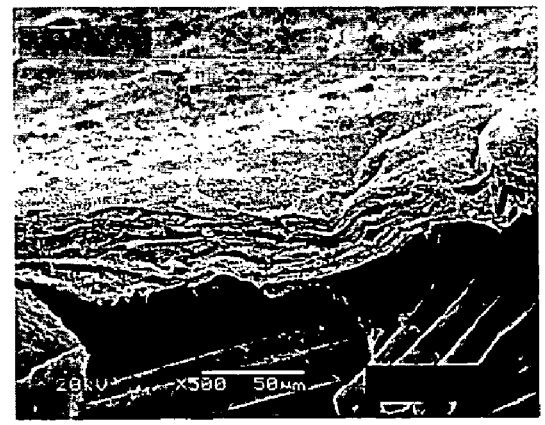
Figure 1:
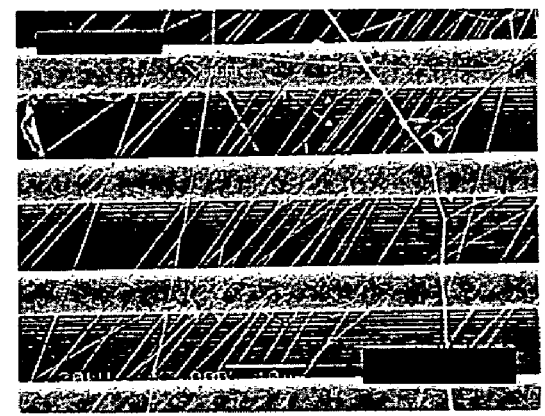

The term "nanofibrillar structure" as used herein means a structure comprising an environment for growth of living cells comprising one or more nanofibers, wherein the structure is defined by a network of one or more nanofibers. In some embodiments, the nanofibrillar structure comprises a substrate wherein the nanofibrillar structure is defined by a network of one or more nanofibers deposited on a surface of the substrate. The nanotopography, the topography of the nanofiber network and the arrangement of the nanofibers of the nanofiber network in space, of the nanofibrillar structure is engineered to provide an in vitro biomimetic substratum that is more tissue compatible for the promotion of homotypic or heterotypic cell growth and/or cell differentiation in single layer or multi-layered cell culture. The nanofibrillar structures may be layered to form a multi-layered nanofibrillar assembly, cellular array, or tissue structure.

The term "nanofiber" as used herein means a polymer fine fiber comprising a diameter of about 1000 nanometers or less. The polymer is preferably a non-cytotoxic polymer. The polymer may be water soluble or water insoluble. The polymer may be biodegradable and/or biodissolvable. The polymer may be a polyester or polyamide. The polyester may be an aliphatic polyester including, but not limited to polylactide, poly(glycolate), poly(ε-caprolactone), and copolymers thereof. The polyamide may be a polycaprolactam, nylon 6, a nylon 66, nylon 6 12 or other nylon material.

The nanofiber may comprise a lipid or lipophilic molecule including, but not limited to, lysophosphatidylcholine, phosphatidylcholine, sphingomyelin, cholesterol, and mixtures thereof. The nanofiber may comprise one or more bioactive molecules. Preferably one of the bioactive molecules is a peptide, polypeptide, lipid, carbohydrate, polysaccharide, amino acid, nucleotide, nucleic acid, polynucleotide, or hybrid molecule thereof. The nanofiber may comprise one or more alcohol, aldehyde, amino, carboxy, sulphydryl or photoactivatable functional groups. Preferably the photoactivatable group is a carbene or nitrene.

The nanofiber may comprise one or more growth factors and/or differentiation factors. The nanofiber may release one or more growth factors and/or differentiation factors. The rate of release is determined by the rate of degradation and/or dissolution of the nanofiber.

The term "network" as used herein means a random or oriented distribution of nanofibers in space that is controlled to form an interconnecting net with spacing between fibers selected to promote growth and culture stability. The network has small spaces between the fibers comprising the network forming pores or channels in the network. The pores or channels have a diameter of about 0.01 microns to about 25 microns, preferably about 2 microns to about 10 microns, through a thickness. A network may comprise a single layer of nanofibers, a single layer formed by a continuous nanofiber, multiple layers of nanofibers, multiple layers formed by a continuous nanofiber, or mat. The network may be unwoven or net. A network may have a thickness of about the diameter of a single nanofiber to about 2000 nm. Physical properties of the network including, but not limited to, texture, rugosity, adhesivity, porosity, solidity, elasticity, geometry, interconnectivity, surface to volume ratio, fiber diameter, fiber solubility/insolubility, hydrophilicity/hydrophobicity, fibril density, and fiber orientation may be engineered to desired parameters.

The term "substrate" as used herein means any surface on which nanofiber or network of nanofibers is deposited. The substrate may be any surface that offers structural support for the deposited network of nanofibers. The substrate may comprise glass or plastic. Preferably the plastic is non-cytotoxic. The substrate may be a film or culture container.

The substrate may be water soluble or water insoluble. A substrate that is water soluble is preferably a polyvinyl alcohol film. The substrate may be porous or non-porous. Porosity of the substrate is determined by cellular penetration. A cell is able to penetrate a porous substrate but is not able to penetrate a non-porous substrate. Preferably the pores in a porous substrate have a diameter of about 2 μm to about 10 μm. The substrate may be biodegradable and/or biodissolvable. Preferably the substrate is biocompatible.

The substrate may comprise one or more bioactive molecules. Preferably one of the bioactive molecules is a peptide, polypeptide, lipid, carbohydrate, polysaccharide, amino acid, nucleotide, nucleic acid, polynucleotide, or hybrid molecule thereof. The substrate may comprise one or more alcohol, aldehyde, amino, carboxy, sulphydryl or photoactivatable functional groups. Preferably the photoactivatable group is a carbene or nitrene. The substrate may comprise one or more growth factors and/or differentiation factors. The substrate may release one or more growth factors and/or differentiation factors. The rate of release is determined by the rate of dissolution or degradation of the substrate.

The term "spacer" as used herein means a layer separating a nanofiber or nanofiber network from a surface of a substrate or a surface of a first nanofibrillar structure from a surface of a second nanofibrillar structure such that the structures are separated by the diameter or thickness of the spacer. The spacer may comprise a polymer fine fiber or film. Preferably the film has a thickness of about 10 microns to about 50 microns. The spacer may comprise a polymer including cellulose, starch, polyamide, polyester, or polytetrafluoroehtylene. The fine fiber may comprise a microfiber. A microfiber is a polymer fine fiber comprising a diameter of about 1.0 μm to about 10 μm. The microfiber may be unwoven or net.

The spacer may be water soluble or water insoluble. The spacer may be porous or non-porous. Porosity of the spacer is determined by cellular penetration. A cell is able to penetrate a porous spacer but is not able to penetrate a non-porous spacer. The spacer may be biodegradable and/or biodissolvable. Preferably the spacer is biocompatible.

The spacer may comprise one or more bioactive molecules. Preferably one of the bioactive molecules is a peptide, polypeptide, lipid, carbohydrate, nucleotide, nucleic acid, polynucleotide, polysaccharide, amino acid, or hybrid molecule thereof. The spacer may comprise one or more alcohol, aldehyde, amino, carboxy, sulphydryl or photoactivatable functional groups. Preferably the photoactivatable group is a carbene or nitrene. The spacer may comprise one or more growth factors and/or differentiation factors. The spacer may release one or more growth factors and/or differentiation factors. The rate of release is determined by the rate of dissolution or degradation of the spacer.

The term "bioactive molecule" as used herein means a molecule that has an effect on a cell or tissue. The term includes human or veterinary therapeutics, nutraceuticals, vitamins, salts, electrolytes, amino acids, peptides, polypeptides, proteins, carbohydrates, lipids, polysaccharides, nucleic acids, nucleotides, polynucelotides, glycoproteins, lipoproteins, glycolipids, glycosaminoglycans, proteoglycans, growth factors, differentiation factors, hormones, neurotransmitters, pheromones, chalones, prostaglandins, immunoglobulins, monokines and other cytokines, humectants, minerals, electrically and magnetically reactive materials, light sensitive materials, anti-oxidants, molecules that may be metabolized as a source of cellular energy, antigens, and any molecules that can cause a cellular or physiological response. Any combination of molecules can be used, as well as agonists or antagonists of these molecules. Glycoaminoglycans include glycoproteins, proteoglycans, and hyaluronan. Polysaccharides include cellulose, starch, alginic acid, chytosan, or hyaluronan. Cytokines include, but are not limited to, cardiotrophin, stromal cell derived factor, macrophage derived chemokine (MDC), melanoma growth stimulatory activity (MGSA), macrophage inflammatory proteins 1 alpha (MIP-1 alpha), 2, 3 alpha, 3 beta, 4 and 5, interleukin (IL) 1, IL-2, IL-3, IL-4, IL-5, IL-6, IL-7, IL-8, IL-9, IL-10, IL-11, IL-12, IL-13, TNF-alpha, and TNF-beta. Immunoglobulins useful in the present invention include, but are not limited to, IgG, IgA, IgM, IgD, IgE, and mixtures thereof. Amino acids, peptides, polypeptides, and proteins may include any type of such molecules of any size and complexity as well as combinations of such molecules. Examples include, but are not limited to, structural proteins, enzymes, and peptide hormones.

The term bioactive molecule also includes fibrous proteins, adhesion proteins, adhesive compounds, deadhesive compounds, and targeting compounds. Fibrous proteins include collagen and elastin. Adhesion/deadhesion compounds include fibronectin, laminin, thrombospondin and tenascin C. Adhesive proteins include actin, fibrin, fibrinogen, fibronectin, vitronectin, laminin, cadherins, selectins, intracellular adhesion molecules 1, 2, and 3, and cell-matrix adhesion receptors including but not limited to integrins such as $\alpha_5\beta_1$, $\alpha_6\beta_1$, $\alpha_7\beta_1$, $\alpha_4\beta_2$, $\alpha_2\beta_3$, and $\alpha_6\beta_4$.

The term bioactive molecule also includes leptin, leukemia inhibitory factor (LIF), RGD peptide, tumor necrosis factor alpha and beta, endostatin, angiostatin, thrombospondin, osteogenic protein-1, bone morphogenic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18.

The term "growth factor" as used herein means a bioactive molecule that promotes the proliferation of a cell or tissue. Growth factors useful in the present invention include, but are not limited to, transforming growth factor-alpha. (TGF-alpha), transforming growth factor-beta. (TGF-beta), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof. Some growth factors may also promote differentiation of a cell or tissue. TGF, for example, may promote growth and/or differentiation of a cell or tissue. Some preferred growth factors include VEGF, NGFs, PDGF-AA, PDGF-BB, PDGF-AB, FGFb, FGFa, and BGF.

The term "differentiation factor" as used herein means a bioactive molecule that promotes the differentiation of cells. The term includes, but is not limited to, neurotrophin, colony stimulating factor (CSF), or transforming growth factor. CSF includes granulocyte-CSF, macrophage-CSF, granulocyte-macrophage-CSF, erythropoietin, and IL-3. Some differentiation factors may also promote the growth of a cell or tissue. TGF and IL-3, for example, may promote differentiation and/or growth of cells.

The term "adhesive compound" as used herein means a bioactive molecule that promotes attachment of a cell to a fiber surface comprising the adhesive compound. Examples of adhesive compounds include, but are not limited to, fibronectin, vitronectin, and laminin.

The term "deadhesive compound" as used herein means a bioactive molecule that promotes the detachment of a cell from a fiber comprising the deadhesive compound. Examples of deadhesive compounds include, but are not limited to, thrombospondin and tenascin C.

The term "targeting compound" as used herein means a bioactive molecule that functions as a signaling molecule inducing recruitment and/or attachment of cells to a fiber comprising the targeting compound. Examples of targeting compounds and their cognate receptors include attachment peptides including RGD peptide derived from fibronectin and integrins, growth factors including EGF and EGF receptor, and hormones including insulin and insulin receptor.

The term "lipid" as used herein means an organic molecule that is insoluble in water but tends to dissolve in nonpolar organic solvents. The term includes lipophilic molecules, including, but not limited to plant and animal triglycerides, sterols, phosphatidylcholine materials, including lysophosphatidylcholine, phosphatidylcholine, sphingomyelin, and cholesterol.

The phrase "adapted for insertion" as used herein means manufactured or fabricated for use in or to the dimensions of a culture container or resizing for use in or to the dimensions of a culture container including, for example, cutting down to size or cutting a piece from a sheet, roll, or mat to a size suitable for insertion into a culture container.

The term "culture container" as used herein means a receptacle for holding media for culturing a cell or tissue. The culture container may be glass or plastic. Preferably the plastic is non-cytotoxic. The term culture container includes, but is not limited to, single and multiwell culture plates, chambered and multi-chambered culture slides, coverslips, cups, flasks, tubes, bottles, roller bottles, spinner bottles, perfusion chambers, bioreactors and fermenters.

The term "mat" as used herein means a densely interwoven, tangled or adhered mass of nanofibers. The distribution of nanofibers in the mat may be random or oriented. A mat may be unwoven or net. A mat may or may not be deposited on a substrate. A mat has a thickness of about 100 to about 1000 nm.

II. Modes for Carrying Out the Invention

A. Improved Nanofiber

One aspect of the invention provides an improved nanofiber comprising a lipid. The nanofiber preferably has a diameter of less than about 1000 nm. In an embodiment, the nanofiber has a diameter of about 50 to about 1000 nanometers The improved nanofiber is useful in a variety of applications, including cell culture and tissue engineering.

i. Polymer and Polymer Systems

The improved nanofiber preferably comprises a non-cytotoxic polymer. The polymer may be water soluble or water insoluble. The polymer may be biodegradable and/or biodissolvable. The polymer may comprise a first polymer and a second, but different polymer (differing in polymer type, molecular weight or physical property) that is conditioned or treated at elevated temperature.

The polymer blend can be reacted and formed into a single chemical specie or can be physically combined into a blended composition by an annealing process. Annealing implies a physical change, like crystallinity, stress relaxation or orientation. Preferred materials are chemically reacted into a single polymeric specie such that a Differential Scanning Calorimeter analysis reveals a single polymeric material. Such a material, when combined with a preferred additive material, can form a surface coating of the additive on the nanofiber that provides oleophobicity, hydrophobicity or other associated improved stability when contacted with high temperature, high humidity and difficult operating conditions. The fine fiber of the class of materials can have a diameter of about 1000 nm to less than about 5 nanometers. Such fibers can have a smooth surface comprising a discrete layer of the additive material or an outer coating of the additive material that is partly solubilized or alloyed in the polymer surface, or both. Preferred materials for use in the blended polymeric systems include nylon 6; nylon 66; nylon 6-10; nylon (6-66-610) copolymers and other linear generally aliphatic nylon compositions. A preferred nylon copolymer resin (SVP-651) was analyzed for molecular weight by the end group titration. (J. E. Walz and G. B. Taylor, determination of the molecular weight of nylon, Anal. Chem. Vol. 19, Number 7, pp 448-450 (1947). A number average molecular weight ($W_n$) was between 21,500 and 24,800. The composition was estimated by the phase diagram of melt temperature of three component nylon, nylon 6 about 45%, nylon 66 about 20% and nylon 610 about 25%. (Page 286, Nylon Plastics Handbook, Melvin Kohan ed. Hanser Publisher, New York (1995)).

Reported physical properties of SVP 651 resin are:

| -Property | ASTM Method | Units | Typical Value |
| --- | --- | --- | --- |
| Specific Gravity | D-792 | — | 1.08 |
| Water Absorption (24 hr immersion) | D-570 | % | 2.5 |
| Hardness | D-240 | Shore D | 65 |
| Melting Point | DSC | °C.(°F.) | 154 (309) |
| Tensile Strength @ Yield | D-638 | MPa (kpsi) | 50 (7.3) |
| Elongation at Break | D-638 | % | 350 |
| Flexural Modulus | D-790 | MPa (kpsi) | 180 (26) |
| Volume Resistivity | D-257 | ohm-cm | $10^{12}$ |

A polyvinyl alcohol having a hydrolysis degree of from 87 to 99.9+% can be used in such polymer systems. These are preferably crosslinked, and they are most preferably crosslinked and combined with substantial quantities of the oleophobic and hydrophobic additive materials.

The polymer may be a single polymeric material optionally combined with an additive composition to improve fiber lifetime or operational properties. The preferred polymers useful in this aspect of the invention include nylon polymers, polyvinylidene chloride polymers, polyvinylidene fluoride polymers, polyvinyl alcohol polymers and, in particular, those listed materials when combined with strongly oleophobic and hydrophobic additives that can result in a microfiber or nanofiber with the additive materials formed in a coating on the fine fiber surface. Again, blends of similar polymers such as a blend of similar nylons, similar polyvinylchloride polymers, blends of polyvinylidene chloride polymers are useful in this invention. Further, polymeric blends or alloys of differing polymers are also contemplated by the invention. In this regard, compatible mixtures of polymers are useful in forming the nanofiber or microfiber materials of the invention.

Additive compositions may be organic or inorganic, metals or non-metals. In an embodiment, the polymer solution comprises from about 0.25 percent to about 70 percent w/w additive composition. In a further embodiment, the additive composition is a bioactive molecule. In another further embodiment, the additive composition is a ceramic. The additive composition may be an optical additive that increases or decreases inherent fiber fluorescence for microscopy. In an embodiment, the optical additive is a quantum dot. In another embodiment, the optical additive minimizes fluorescent background of the fiber by enhancing the signal to noise ratio. Examples of optical additives include, but are not limited to quantum dots or Fluoroblok™ (Bectin Dickinson, Franklin Lakes, N.J.).

Polymer materials that can be used in the polymeric compositions of the invention include both addition polymer and condensation polymer materials such as polyolefin, polyacetal, polyamide, polyester, cellulose ether and ester, polyalkylene sulfide, polyarylene oxide, polysulfone, modified polysulfone polymers and mixtures thereof. Preferred materials that fall within these generic classes include polyethylene, poly(ε-caprolactone), poly(lactate), poly(glycolate), polypropylene, poly(vinylchloride), polymethylmethacrylate (and other acrylic resins), polystyrene, and copolymers thereof (including ABA type block copolymers), poly(vinylidene fluoride), poly(vinylidene chloride), polyvinyl alcohol in various degrees of hydrolysis (87% to 99.5%) in crosslinked and non-crosslinked forms. Preferred addition polymers tend to be glassy (a Tg greater than room temperature). This is the case for polyvinylchloride and polymethylmethacrylate, polystyrene polymer compositions or alloys or low in crystallinity for polyvinylidene fluoride and polyvinyl alcohol materials.

Aliphatic polyesters such as poly(ε-caprolactone), poly(lactate), poly(glycolate), and their copolymers are biodegradable, and biocompatible and among the few synthetic polymers approved by the Food and Drug Administration (FDA) for certain human clinical applications such as surgical sutures and some implantable devices. In an embodiment, the nanofibers are fabricated from an aliphatic polyester suitable for in vivo human application. Preferably the polyester is poly(ε-caprolactone), poly(lactate) or poly(glycolate). In an embodiment, the nanofibers are fabricated from a polymer solution comprising at least about 10% poly(ε-caprolactone) w/w in chloroform. In another embodiment, the nanofibers are fabricated from a polymer solution comprising at least about 15% poly(ε-caprolactone) w/w in chloroform.

One class of polyamide condensation polymers are nylon materials. The term "nylon" is a generic name for all long chain synthetic polyamides. Typically, nylon nomenclature includes a series of numbers such as in nylon-6,6 which indicates that the starting materials are a $C_6$ diamine and a $C_6$ diacid (the first digit indicating a $C_6$ diamine and the second digit indicating a $C_6$ dicarboxylic acid compound). Another nylon can be made by the polycondensation of epsilon caprolactam in the presence of a small amount of water. This reaction forms a nylon-6 (made from a cyclic lactam—also known as epsilon-aminocaproic acid) that is a linear polyamide. Further, nylon copolymers are also contemplated. Copolymers can be made by combining various diamine compounds, various diacid compounds and various cyclic lactam structures in a reaction mixture and then forming the nylon with randomly positioned monomeric materials in a polyamide structure. For example, a nylon 6,6-6,10 material is a nylon manufactured from hexamethylene diamine and a $C_6$ and a $C_{10}$ blend of diacids. A nylon 6-6,6-6,10 is a nylon manufactured by copolymerization of epsilon aminocaproic acid, hexamethylene diamine and a blend of a $C_6$ and a $C_{10}$ diacid material.

Block copolymers are also useful in the process of this invention. With such copolymers the choice of solvent swelling agent is important. The selected solvent is such that both blocks were soluble in the solvent. One example is a ABA (styrene-EP-styrene) or AB (styrene-EP) polymer in methylene chloride solvent. If one component is not soluble in the solvent, it will form a gel. Examples of such block copolymers are KRATON® type of AB and ABA block polymers including styrene/butadiene and styrene/hydrogenated butadiene(ethylene propylene), PEBAX® type of epsilon-caprolactam/ethylene oxide, SYMPATEX® polyester/ethylene oxide and polyurethanes of ethylene oxide and isocyanates.

Addition polymers like polyvinylidene fluoride, syndiotactic polystyrene, copolymer of vinylidene fluoride and hexafluoropropylene, polyvinyl alcohol, polyvinyl acetate, amorphous addition polymers, such as poly(acrylonitrile) and its copolymers with acrylic acid and methacrylates, polystyrene, poly(vinyl chloride) and its various copolymers, poly (methyl methacrylate) and its various copolymers, can be solution spun with relative ease because they are soluble at low pressures and temperatures. However, highly crystalline polymer like polyethylene and polypropylene require high temperature, high pressure solvent if they are to be solution spun. Therefore, solution spinning of the polyethylene and polypropylene is very difficult. Electrostatic solution spinning is one method of making nanofibers and microfiber.

We have also found a substantial advantage to forming polymeric compositions comprising two or more polymeric materials in polymer admixture, alloy format or in a crosslinked chemically bonded structure. We believe such polymer compositions improve physical properties by changing polymer attributes such as improving polymer chain flexibility or chain mobility, increasing overall molecular weight and providing reinforcement through the formation of networks of polymeric materials.

In one embodiment of this concept, two related polymer materials can be blended for beneficial properties. For example, a high molecular weight polyvinylchloride can be blended with a low molecular weight polyvinylchloride. Similarly, a high molecular weight nylon material can be blended with a low molecular weight nylon material. Further, differing species of a general polymeric genus can be blended. For example, a high molecular weight styrene material can be blended with a low molecular weight, high impact polystyrene. A Nylon-6 material can be blended with a nylon copolymer such as a Nylon-6; 6,6; 6,10 copolymer. Further, a polyvinyl alcohol having a low degree of hydrolysis such as a 87% hydrolyzed polyvinyl alcohol can be blended with a fully or super hydrolyzed polyvinyl alcohol having a degree of hydrolysis between 98 and 99.9% and higher. All of these materials in admixture can be crosslinked using appropriate crosslinking mechanisms. Nylons can be crosslinked using crosslinking agents that are reactive with the nitrogen atom in the amide linkage. Polyvinyl alcohol materials can be crosslinked using hydroxyl reactive materials such as monoaldehydes, such as formaldehyde, ureas, melamine-formaldehyde resin and its analogues, boric acids and other inorganic compounds, dialdehydes, diacids, urethanes, epoxies and other known crosslinking agents. Crosslinking technology is a well known and understood phenomenon in which a crosslinking reagent reacts and forms covalent bonds between polymer chains to substantially improve molecular weight, chemical resistance, overall strength and resistance to mechanical degradation.

Electrospinning produces a population of nanofibers that may differ in diameter, typically from about 5 nm to about 1000 nm. A preferred mode of the invention involves a polymeric material combined with an additive composition that influences packing of the polymer such that electrospinning of the polymer results in the production of a population of nanofibers having a greater number or percentage of thin fibers as compared to a population of nanofibers electrospun form a polymer solution not containing the additive composition. In an embodiment, the polymer solution comprises from about 0.25% to about 15% w/w additive composition. In another embodiment, the polymer solution comprises from about 1% to about 10% w/w additive composition.

Thin fibers preferably have a diameter of about 5 nm to about 600 nm. In an embodiment, thin fibers have a diameter of about 50 nm to about 400 nm. In another embodiment, thin fibers have a diameter of about 300 nm. In another embodiment, thin fibers have a diameter of about 5 nm to about 200 nm. In another embodiment, thin fibers have a diameter of about 5 nm to about 100 nm. In another embodiment, thin fibers have a diameter of about 5 nm to about 50 nm.

Nanofibers having a smaller diameter provide a surface that promotes multipoint attachments between nanofibers and cells, a characteristic of cell attachment to the extracellular matrix in vivo. Preferably at least about 25% of the population of lipid containing nanofibers is thin fibers. In an embodiment, at least about 30% percent of the population of lipid containing nanofibers are thin fibers. In another embodiment, at least about 40% of the polydisperse plurality of lipid containing nanofibers is thin fibers. In another embodiment, at least about 50% of polydisperse plurality of lipid containing nanofibers is thin fibers. In another embodiment, at least about 60% of polydisperse plurality of lipid containing nanofibers is thin fibers. In another embodiment, at least about 70% of polydisperse plurality of lipid containing nanofibers is thin fibers.

Preferably the additive composition is non-cytotoxic. In an embodiment, the additive composition that influences packing of the polymer is a bioactive molecule. The bioactive molecule may be a lipid. Preferably the lipid is lysophosphatidylcholine, phosphatidylcholine, sphingomyelin, cholesterol, and mixtures thereof.

The additive composition may or may not affect the activity of cells, including migration or cell attachment to the nanofibers. In an embodiment, a nanofiber comprising the additive composition does not affect the activity of cells.

Preferably, the additive composition comprises one or more bioactive molecules. One or more of the bioactive molecules may be a lipid. Preferably the lipid is cholesterol. In another embodiment, a nanofiber comprising the additive composition may affect the activity of cells. Such a nanofiber may induce cell migration or enhance attachment of cells to the nanofiber. Preferably the additive composition comprises one or more bioactive molecules. One or more bioactive molecules may be a lipid. In an embodiment, the lipid is lysophosphatidylcholine, phosphatidylcholine, sphingomyelin, or mixtures thereof. In another embodiment, the additive composition comprises cholesterol and one or more bioactive molecules that affect the activity of cells including growth factors, differentiation factors, and/or adhesive proteins.

The polymer or polymer system may comprise one or more bioactive molecules including but not limited to lipids or lipophilic molecules, fibrous proteins, adhesion proteins, growth factors, and differentiation factors. Preferably at least one of the bioactive molecules comprises a lipid. In an embodiment, the lipid molecules may function as signaling molecules inducing recruitment and attachment of cells to the fiber. The lipid molecules may also cause the cells to proliferate or differentiate. Nanofibers comprising bioactive molecules, such as lipids, that promote guided migration and tight attachment of cells which may be used in vivo or ex vivo for applications including wound repair, growth of artificial skin, veins, arteries, tendons, ligaments, cartilage, heart valves organ cultures, treatment of burns, and bone grafts. Preferably the lipid is lysophosphatidylcholine, phosphatidylcholine, sphingomyelin, or mixtures thereof.

Preferably one or more of the bioactive molecules is a growth factor, differentiation factor, fibrous protein, and/or adhesive protein. Preferably the growth factor is VEGF, bone morphogenic factor β, EGF, PDGF, NGF, FGF, IGF, or TGF. Preferably the differentiation factor is neurotrophin, CSF, or TGF. Preferably the differentiation factor is neurotrophin, CSF, or TGF.

The polymer systems of the invention have adhering characteristic such that when contacted with a cellulosic, polyvinyl, polyester, polystyrene, or polyamide substrate adheres to the substrate with sufficient strength such that it is securely bonded to the substrate and can resist delaminating effects associated with mechanical stresses. The nanofibers of the invention may be used to construct three-dimensional functional tissues, including muscle and tendon. In such a mode, the polymer material must stay attached to the substrate while undergoing mechanical stresses associated with, for example, contraction of a muscle or tendon. Adhesion of the nanofiber to the substrate can arise from solvent effects of fiber formation as the fiber is contacted with the substrate or the post treatment of the fiber on the substrate with heat or pressure. However, polymer characteristics appear to play an important role in determining adhesion, such as specific chemical interactions like hydrogen bonding, contact between polymer and substrate occurring above or below Tg, and the polymer formulation including additives. Polymers plasticized with solvent or steam at the time of adhesion can have increased adhesion.

ii. Functionalized Surfaces

Functional groups may be incorporated at the outside surface of the nanofibers. These functionalized surfaces may be reacted to bind a peptide, polypeptide, lipid, carbohydrate, polysaccharide, amino acid, nucleotide, nucleic acid, polynucleotide, or other bioactive molecule to the surface of the nanofiber. In an embodiment, the functionalized surfaces of the nanofiber are reacted to bind one or more bioactive molecules. Preferably one or more of the bioactive molecules is a growth factor, differentiation factor, adhesive protein, or bioactive peptide derived from an adhesive protein. Preferably the growth factor is VEGF, bone morphogenic factor β, EGF, PDGF, NGF, FGF, IGF, or TGF. Preferably the differentiation factor is neurotrophin, CSF, or TGF. Preferably the differentiation factor is neurotrophin, CSF, or TGF. Preferably the bioactive peptide is RGD peptide.

In an embodiment, functional groups are deposited on the outside surface of a nanofiber by plasma deposition. Plasma deposition creates local plasmas at the surface of the nanofiber. The treated surface is then reacted with gaseous molecules, such as allylamine and/or allyl alcohol, in a reaction chamber. In another embodiment, functional groups are introduced onto the surface of the nanofibers during the electrospinning process. Dodecyl amine, dodecyl aldehyde, dodecyl thiol, or dodecyl alcohol may be added to the polymer solution. The polymer solution is than electrospun into nanofibers in which a portion of the added amines, aldehydes, sulphydryl, or alcohol moieties, respectively, are exposed on the outside surface of the nanofibers.

iii. Fluorescent Marker

The nanofibers may comprise a fluorescent marker. The fluorescent marker allows, for example, visualization of a nanofiber, identification of specific nanofibers within a nanofiber blend, identification of a chemical or physical property of a nanofiber, and evaluation of the degradation of and/or redistribution of implantable nanofibers and/or structures comprising nanofibers, including multi-layered assemblies useful for engineering tissue, which can be degraded and transported to other regions distant from the original site of implantation. The fluorescent marker may be photobleachable or non-photobleachable. The fluorescent marker may be pH sensitive or pH insensitive. Preferably the fluorescent marker is non-cytotoxic.

The fluorescent marker may comprise an organic dye fluorophore including, but not limited to, TEXAS RED®, BIODIPY®, OREGON GREEN®, ALEXA FLUOR®, fluorescein, CASCADE BLUE®, DAPOXYL®, coumarin, Rhodamine, N-methyl-4-hydrazine-7-nitrobenzofurazan, dansyl ethylenediamine, dansyl cadaverine, dansyl hydrazine, or mixtures thereof. More information on these and other suitable organic dye fluorophores may be found at www-probes-com (Molecular Probes, Eugene, Oreg.). In an embodiment, the fluorophore is added to the polymer prior to electrospinning of a nanofiber. In another embodiment, the fluorophore is conjugated to a nanofiber via a functional group incorporated at the surface of the nanofiber. In another embodiment, the fluorophore is conjugated to a bioactive molecule that is attached to a nanofiber.

The fluorescent marker may comprise colloidal inorganic semiconductor nanocrystals. In an embodiment the nanocrystals comprise a CdSe core and ZnS cap. In another embodiment the nanocrystals comprise quantum dots. More information on nanocrystals and quantum dots may be found at www-evidenttech-com and www-quantumdots-com. The absorption spectra of the nanocrystal may be broad, extending from ultraviolet to a cutoff in the visible spectrum. The emission spectra may be narrow, preferably 20-40 nm full width at half maximum centered at a wavelength that is characteristic of the particle size of the selected nanocrystal. Preferably the nanocrystals are photochemically stable and/or non-cytotoxic.

The fluorescent marker may be used to identify a chemical and/or physical property of the nanofiber. In an embodiment, a fluorescent marker is assigned to a chemical or physical property of the nanofiber and the nanofiber is labeled with the assigned fluorescent marker. Such chemical and physical properties include, but are not limited to, fiber diameter, bioactive molecules, functional groups, dissolution or degradation rate of fiber, composition of polymer comprising the nanofiber, hydrophobicity or hydrophilicity of the fiber; solubility of the polymer comprising the nanofiber, toxicity of the polymer, toxicity of bioactive molecules, or combinations thereof. In an embodiment, the bioactive molecule is a growth factor, differentiation factor, an adhesion molecule, or mixtures thereof. Labeling nanofibers with a specific fluorescent marker, for example, allows for the identification of each type of fiber within a nanofiber blend or cellular array. A nanofiber may be labeled with more than one fluorescent marker in order to identify multiple chemical and/or physical properties of the nanofiber.

The fluorescent marker may comprise bioactive fluorescent probes to determine changes in a biochemical environment. In an embodiment, the nanofiber may comprise a fluorescent marker wherein the fluorescence or fluorescent intensity of the marker is dependent upon ion concentration. Such an ion sensing element is useful to detect changes in ion concentration including pH and calcium, sodium, or phosphate flux. In an embodiment, the fluorescent marker comprises SNARF, SNAFL, calcium green, or mixtures thereof. In another embodiment, the nanofiber contains dyes capable of changing their fluorescent properties as a result of complexion with other molecules.

iv. Applications

The improved nanofiber may be used in many known applications employing nanofibers including, but not limited to, filter applications, computer hard drive applications, and pharmaceutical applications. The improved nanofiber is useful in a variety of biological applications, including cell culture, tissue culture, and tissue engineering applications. In one application, a nanofibrillar structure for cell culture and tissue engineering may be fabricated using the improved nanofiber. In an embodiment, the nanofibrillar structure comprises one or more improved nanofibers, wherein the nanofibrillar structure is defined by a network of one or more improved nanofibers. In another embodiment, the nanofibrillar structure comprises one or more improved nanofibers and a substrate wherein the nanofibrillar structure is defined by a network of one or more improved nanofibers deposited on a surface of the substrate.

In another application, a growth media for cell culture may be prepared using the improved nanofiber. In an embodiment, the growth media comprises a matrix of nanofibers in the form of a mat, roll, or sheet that may be adapted for insertion into a culture container. In another embodiment, the growth media comprises a matrix of nanofibers that is deposited onto a surface of a culture container or added as a fibrous mesh to the culture container.

In another application, the improved nanofiber may be sprayed or spun onto a three-dimensional structure suitable for cell or tissue culture. The resultant three-dimensional structure is returned to a cell culture apparatus for continued growth where the electrospun fiber structure serves as a platform for growth of the cells. In a further application, the improved nanofibers may be electrospun into nonwoven mesh and/or braids for the layered construction of three-dimensional matrices to serve as templates for tissue regeneration. In a further application, the improved nanofibers may be used as a cell culture medium in high throughput drug analysis and drug sensitivity analysis to increase the number of cells per well providing higher signal for detection of cell response. In another further application, the improved nanofibers may be used as a cell culture medium in high throughput drug analysis, drug sensitivity analysis, and other therapeutic schemes where the nanofibers provide an environment for the cells to more closely mimic the in vivo nature of the cells in an ex vivo environment.

B. Nanofibrillar Structure

Another aspect of the invention is a nanofibrillar structure. The nanofibrillar structure comprises an environment for growth of living cells comprising one or more nanofibers, wherein the nanofibrillar structure is defined by a network of one or more nanofibers. In some embodiments, the nanofibrillar structure comprises a substrate wherein the nanofibrillar structure is defined by a network of one or more nanofibers deposited on a surface of the substrate. The nanotopography of the nanofibrillar structure may be engineered to provide a more tissue-like substratum for the promotion of homotypic or heterotypic cell growth and/or cell differentiation in single layer or multi-layered cell culture.

i. Nanofiber Network

The nanofibers comprising the nanofibrillar structure may comprise a polymer or polymer system as described above for the improved nanofiber. In an embodiment, the nanofibers are fabricated from a polymer suitable for in vivo human application. The nanofiber may be fabricated by many techniques, including preferred electrospinning techniques. Polymer selection and/or the process by which the nanofibers are fabricated and/or directed and oriented onto a substrate allow for specific selection and manipulation of physical properties of the nanofiber network. Physical properties of a growth surface, including fiber size, fiber diameter, fiber spacing, matrix density, fiber texture and elasticity, have been demonstrated to be important considerations for organizing the cytoskeletal networks in cells and the exposure of cell signaling motifs in extracellular matrix proteins (Meiners, S. and Mercado, M. L., 2003, *Mol. Neurobiol.*, 27(2), 177-196). Physical properties of the nanofiber network that may be engineered to desired parameters include, but are not limited to, texture, rugosity, adhesivity, porosity, solidity, elasticity, geometry, interconnectivity, surface to volume ratio, fiber size, fiber diameter, fiber solubility/insolubility, hydrophilicity/hydrophobicity, and fibril density.

One or more of the physical properties of the nanofibrillar structure may be varied and/or modified to create a specifically defined environment for cell growth and/or differentiation. For example, porosity of the nanofibrillar structure may be engineered to enhance diffusion of ions, metabolites, and/or bioactive molecules and/or allow cells to penetrate and permeate the nanofibrillar structure to grow in an environment that promotes multipoint attachments between the cells and the nanofiber network. Interconnectivity of the nanofiber network of the nanofibrillar structure may be engineered to facilitate cell-cell contacts. Elasticity of the nanofiber network of the nanofibrillar structure may be increased or decreased by adding a bioactive molecule to the polymer solution from which the nanofibers are fabricated. In an embodiment, the bioactive molecule is a lipid. In a further embodiment the lipid is cholesterol.

Texture and rugosity of the nanofibrillar structure may be engineered to promote attachment of cells. Homogeneous or heterogeneous nanofiber compositions may be selected to optimize growth or differentiation activity of the cells. For example, the nanofibrillar structure may be comprised of multiple nanofibers having different diameters and/or multiple nanofibers fabricated from different polymers. Solubility or insolubility of the nanofibers of the nanofiber network may be engineered to control the release of bioactive molecules from nanofibrillar structure. In an embodiment, the rate of release of bioactive molecules is determined by the rate of biodegradation or biodissolution of the nanofibers of the nanofiber network. Hydrophobicity and hydrophilicity of the nanofiber network of the nanofibrillar structure may be engineered to promote specific cell spacing. Solidity of the nanofibrillar structure may be engineered to promote cell growth and/or differentiation. In an embodiment, the nanofibrillar structure has a solidity of about 3 percent to about 70 percent. In another embodiment, the nanofibrillar structure has a solidity of about 3 percent to about 50 percent. In another embodiment, the nanofibrillar structure has a solidity of about 3 percent to about 30 percent. In another embodiment, the nanofibrillar structure has a solidity of about 3 percent to about 10 percent. In another embodiment, the nanofibrillar structure has a solidity of about 3 percent to about 5 percent. In another embodiment, the nanofibrillar structure has a solidity of about 10 percent to about 30 percent.

The electrospinning process uses an electric field to control the formation and deposition of polymers. A polymer solution is injected with an electrical potential. The electrical potential creates a charge imbalance that leads to the ejection of a polymer solution stream from the tip of an emitter such as a needle. The polymer jet within the electric field is directed toward a grounded substrate, during which time the solvent evaporates and fibers are formed. The resulting single continuous filament collects as a nonwoven fabric on the substrate.

Electrospun nanofiber networks may be produced having random or directed orientations. As shown in FIGS. 1A and B, random fibers may be assembled into layered surfaces. In an embodiment, the nanofibers of the invention comprise a random distribution of fine fibers that can be bonded to form an interlocking network. The nanofiber interlocking networks have relatively small spaces between the fibers. Such spaces typically range, between fibers, of about 0.01 to about 25 microns, preferably about 2 to about 10 microns. Such spaces form pores or channels in the nanofiber network allowing for diffusion of ions, metabolites, proteins, and/or bioactive molecules and/or allowing cells to penetrate and permeate the network and grow in an environment that promotes multipoint attachments between cells and the nanofibers.

As shown in FIG. 1C, nanofiber networks may be electrospun in an oriented manner. Such oriented electrospinning allows for the fabrication of a nanofiber network comprising a single layer of nanofibers or a single layer formed by a continuous nanofiber wherein the network has a height of the diameter of a single nanofiber. Physical properties including porosity, solidity, fibril density, texture, rugosity, and fiber orientation of the single layer network may be selected by controlling the direction and/or orientation of the nanofiber onto the substrate during the electrospinning process. Preferably the pore size allows cells to penetrate and/or migrate through the single layer nanofiber network. In an embodiment, the space between fibers is about 0.01 to about 25 microns. In another embodiment, the space between fibers is about 2 to about 10 microns.

Layering of individual single layer networks form channels in the nanofibrillar structure allowing diffusion of ions, metabolites, proteins, and/or bioactive molecules and allowing cells to penetrate the nanofibrillar structure and grow in an environment that promotes multipoint attachments between the cells and the nanofiber network.

Phase separation techniques may also be used to fabricate the nanofibrillar structure. The phase separation process typically includes polymer dissolution, phase separation and gelatin, solvent extraction from the gel with water, freezing, and then freeze drying under a vacuum. A typical procedure may be used as follows: polymer is added to solvent such as THF was added to make a solution about 1% (wt/v) to 15% (wt/v). The solution is stirred until uniform. Polymer solution (prewarmed to 50° C.) is added into a Teflon vial. The vial containing polymer solution is then rapidly chilled to gel. The gel-time depends on temperature, solvent, and the polymer concentration. The gel is kept at temperature for at least 120 minutes. The gel is than immersed into distilled water for solvent exchange for 2 days. Following solvent exchange, the gel is removed from water, dried with filter paper, and frozen at −18° C. The frozen gel is than transferred into a freeze-drying vessel at about −10° C. under vacuum lower than 0.5 mm Hg for 1 week. The dried scaffolds are then maintained in a desiccator.

The nanofibers comprising the nanofibrillar structure may comprise one or more bioactive molecules as described above for the improved nanofiber. The bioactive molecules may be incorporated into the nanofiber network during fabrication of the network or may be attached to a surface of the network via a functional group. In an embodiment, the polymer or polymer system from which the nanofiber is fabricated may comprise one or more of the bioactive molecules including, but not limited to, a lipid, growth factor, differentiation factor, fibrous protein, and adhesive protein. The lipid may be lyso-phosphatidylcholine, phosphatidylcholine, sphingomyelin, or mixtures thereof. Preferably the growth factor is VEGF, bone morphogenic factor β, EGF, PDGF, NGF, FGF, IGF, or TGF. Preferably the differentiation factor is neurotrophin, CSF, or TGF. Preferably the differentiation factor is neurotrophin, CSF, or TGF.

Functional groups may be incorporated onto a surface of the network as described for the improved nanofiber. The functionalized surfaces of the network may be reacted to bind a peptide, polypeptide, lipid, carbohydrate, polysaccharide, nucleotide, nucleic acid, polynucleotide, or other bioactive molecule to the surface of the network. In an embodiment, the functionalized surfaces of the network are reacted to bind one or more bioactive molecules. Preferably one or more of the bioactive molecules is a growth factor, differentiation factor, fibrous protein, and/or adhesive protein. Preferably the growth factor is VEGF, bone morphogenic factor β, EGF, PDGF, NGF, FGF, IGF, or TGF. Preferably the differentiation factor is neurotrophin, CSF, or TGF.

ii. Substrate

Structural properties of the nanofibrillar structure such as strength and flexibility are provided in large part by the substrate on which the nanofiber network is deposited. The substrate may comprise cellulose, glass or plastic. Preferably the plastic is non-cytotoxic. The substrate may be a film or culture container. Preferably the film has a thickness of not more than about 10 to about 1000 microns.

The substrate may be water soluble or water insoluble. A substrate that is water soluble is preferably a polyvinyl alcohol film and can be used with a polyvinyl alcohol fiber matrix. The substrate may be porous or non-porous. Porosity of the substrate is determined by cellular penetration. A cell is able to penetrate a porous substrate but is not able to penetrate a non-porous substrate. Preferably the pores in a porous substrate have a diameter of about 2 μm to about 10 μm. The substrate may be biodegradable and/or biodissolvable. Preferably the substrate is biocompatible.

The substrate may comprise one or more bioactive molecules. The bioactive molecules may be incorporated into the substrate during fabrication of the substrate or may be attached to a surface of the substrate via a functional group. Functional groups may be incorporated onto a surface of the substrate as described for the improved nanofiber. The functionalized surfaces of the substrate may be reacted to bind a peptide, carbohydrate, polysaccharide, lipid, nucleotide, nucleic acid, polynucleotide, or other bioactive molecule to the surface of the substrate.

In an embodiment, the functionalized surfaces of the substrate are reacted to bind one or more bioactive molecules. Preferably one or more of the bioactive molecules is a growth factor, differentiation factor, fibrous protein, and/or adhesive protein. Preferably the growth factor is VEGF, bone morphogenic factor β, EGF, PDGF, NGF, FGF, IGF, or TGF. Preferably the differentiation factor is neurotrophin, CSF, or TGF. Preferably the differentiation factor is neurotrophin, CSF, or TGF. The substrate may release one or more bioactive molecules. The rate of release is determined by the rate of dissolution and/or degradation of the substrate.

iii. Spacer

Structural properties of a nanofibrillar structure, such as strength and flexibility, may be further provided by a spacer. Spacers may also provide sufficient separation between a nanofiber network and a substrate or sufficient separation between two or more nanofibrillar structures to permit cells to penetrate and attach to the nanofibers.

In an embodiment, the spacer comprises a first and second surface wherein the first surface of the spacer contacts a surface of the nanofiber network deposited on a substrate and the second surface of the spacer contacts a surface of the substrate such that the nanofiber network and substrate are separated by the diameter or thickness of the spacer. In another embodiment, the spacer comprises a first and second surface wherein the first surface of the spacer contacts a surface of a first nanofibrillar structure and the second surface of the spacer contacts a surface of a second nanofibrillar structure such that the two nanofibrillar structures are separated by the diameter or thickness of the spacer.

The spacer may comprise a fine fiber or film. Preferably the film has a thickness of not more than about 10 to about 50 microns. The fine fiber may comprise a microfiber. Preferably the microfiber has a diameter of about 1 micron to about 10 microns. The microfiber may be unwoven or net. The microfiber may be fabricated from many polymers including cellulose, polyamide, polyester, and polytetrafluoroethylene.

The spacer may be water soluble or water insoluble. The spacer may be porous or non-porous. Porosity of the substrate is determined by cellular penetration. A cell is able to penetrate a porous spacer but is not able to penetrate a non-porous spacer. Preferably the pores in a porous spacer have a diameter of about 2 μm to about 10 μm. The spacer may be biodegradable and/or biodissolvable. Preferably the spacer is biocompatible.

The spacer may comprise one or more bioactive molecules. The bioactive molecules may be incorporated into the spacer during fabrication of the spacer or may be attached to a surface of the spacer via a functional group. Functional groups may be incorporated onto a surface of the spacer as described for the improved nanofiber. The functionalized surfaces of the spacer may be reacted to bind a peptide, carbohydrate, polysaccharide, lipid, nucleotide, nucleic acid, polynucleotide, or other bioactive molecule to the surface of the spacer.

In an embodiment, the functionalized surfaces of the spacer are reacted to bind one or more bioactive molecules. Preferably one or more of the bioactive molecules is a growth factor, differentiation factor, fibrous protein, and/or adhesive protein. Preferably the growth factor is VEGF, bone morphogenic factor β, EGF, PDGF, NGF, FGF, IGF, or TGF. Preferably the differentiation factor is neurotrophin, CSF, or TGF. Preferably the differentiation factor is neurotrophin, CSF, or TGF. The spacer may release one or more bioactive molecules. The rate of release is determined by the rate of dissolution and/or degradation of the spacer.

iii. Multi-Layered Assembly of Nanofibrillar Structures

A nanofibrillar structure of the invention may be used in a variety of applications, including cell culture and tissue culture applications, high throughput applications for drug discovery, and filtration applications. In one application, the nanofibrillar structure may be utilized singly or layered to form a multi-layered nanofibrillar assembly for cell or tissue culture. The nanofibrillar structures have many in vivo and ex vivo uses including wound repair, growth of artificial skin, veins, arteries, tendons, ligaments, cartilage, heart valves, organ culture, treatment of burns, and bone grafts.

A diverse array of growth environments for a cell or tissue may be constructed by engineering specific chemical and physical properties into the nanofiber network, substrate, and/or spacers comprising the individual nanofibrillar structure and/or sequentially layering individual nanofibrillar structures. Physical properties and/or characteristics of the individual nanofibrillar structure including, but not limited to, texture, rugosity, adhesivity, porosity, solidity, elasticity, geometry, interconnectivity, surface to volume ratio, fiber diameter, fiber solubility/insolubility, hydrophilicity/hydrophobicity, fibril density, and fiber orientation may be varied and/or modified to construct nano- and/or micro-environments that promote one or more selected cellular activities, including growth and/or differentiation. Specific nano- and/or micro-environments may be engineered within individual nanofibrillar structures or within a cellular array comprising two or more layered nanofibrillar structures.

Specific recognition motifs such as peptides, polypeptides, lipids, carbohydrates, amino acids, nucleotides, nucleic acids, polynucleotides, or polysaccharides including, but not limited to, growth factors, differentiation factors, fibrous proteins, adhesive proteins, glycoproteins, functional groups, adhesive compounds, deadhesive compounds, and targeting molecules may be engineered into the nanofibrillar network, substrate, and/or spacers of the individual nanofibrillar structures or multi-layered nanofibrillar assembly either isotropically or as gradients to promote appropriate cellular activity, including cell growth and/or differentiation. Embodiments involving amino acids, peptides, polypeptides, and proteins may include any type of such molecules of any size and complexity as well as combinations of such molecules. Examples include, but are not limited to, structural proteins, enzymes, and peptide hormones.

Many types of cells may be grown on the nanofibrillar structure including, but not limited to, stem cells, committed stem cells, differentiated cells, and tumor cells. Examples of stem cells include, but are not limited to, embryonic stem cells, bone marrow stem cells and umbilical cord stem cells. Other examples of cells used in various embodiments include, but are not limited to, osteoblasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, and neurons. In some embodiments it is unnecessary to pre-select the type of stem cell that is to be used, because many types of stem cells can be induced to differentiate in an organ specific pattern by engineering the physical and/or chemical properties of the individual nanofibrillar structures or multi-layered nanofibrillar assembly by delivering the individual nanofibrillar structures or multi-layered assembly to a given organ. For example, a stem cell may be induced to become a liver cell by engineering the appropriate differentiation and/or growth factors into the nanofibrillar structure or by implanting a nanofibrillar structure comprising stem cells within the liver. Cells in the nanofibrillar structure can serve the purpose of providing cell seeding, producing certain compounds, or both.

Cells useful in the invention may be cultured in vitro, derived from a natural source, genetically engineered, or produced by any other means. Any natural source of prokaryotic or eukaryotic cells may be used. Embodiments in which nanofibrillar structures are implanted in an organism can use cells from the recipient, cells from a nonspecific donor or a donor from a different species, or bacteria or microbial cells. Cells harvested from a source and cultured prior to use are included.

Some embodiments use atypical or abnormal cells such as tumor cells. The physical and/or chemical properties of the nanofibrillar structure, including growth and differentiation factors, on which such cells are grown may be engineered to mimic the native in vivo nano- or micro-environment of the tumor. Tumor cells cultured on nanofibrillar structures can provide more accurate representations of the native tumor environment in the body for the assessment of drug treatments. Growth of tumor cells on nanofibrillar structures of the invention facilitate characterization of biochemical pathways and activities of the tumor, including gene expression, receptor expression, and polypeptide production, in an in vivo-like environment allowing for the development of drugs that specifically target the tumor.

Some embodiments use cells that have been genetically engineered. The engineering involves programming the cell to express one or more genes, repressing the expression of one or more genes, or both. One example of genetically engineered cells useful in the present invention is a genetically engineered cell that makes and secretes one or more desired bioactive molecules. When nanofibrillar structure comprising genetically engineered cells are implanted in an organism, the molecules produced can produce a local effect or a systemic effect, and can include the molecules identified above as possible substances. Cells can also produce antigenic materials in embodiments in which one of the purposes of the nanofibrillar structure is to produce an immune response. Cells may produce substances to aid in the following non-inclusive list of purposes: inhibit or stimulate inflammation; facilitate healing; resist immuno-rejection; provide hormone replacement; replace neurotransmitters; inhibit or destroy cancer cells; promote cell growth; inhibit or stimulate formation of blood vessels; augment tissue; and to supplement or replace skin, synovial fluid, tendons, cartilage, ligaments, bone, muscle, organs, dura, blood vessels, bone marrow, and extracellular matrix.

Genetic engineering can involve, for example, adding or removing genetic material to or from a cell, altering existing genetic material, or both. Embodiments in which cells are transfected or otherwise engineered to express a gene can use transiently or permanently transfected genes, or both. Gene sequences may be full or partial length, cloned or naturally occurring.

In an embodiment, viable cells are deposited on a nanofibrillar structure. Nano- and/or micro-environments that promote cellular activity of a particular cell or tissue may be engineered into the nanofibrillar structure by varying and/or modifying selected physical and/or chemical properties of the nanofiber network. The physical and/or chemical properties may be engineered into the individual nanofibrillar structures as described above. The nanofibrillar structure comprising the cells is cultured under conditions that promote cellular activity, including growth and/or differentiation.

In another embodiment, two or more nanofibrillar structures are layered to form a multi-layered nanofibrillar assembly. Nano- and/or micro-environments that promote cellular activity of a particular cell or tissue may be constructed by layering nanofibrillar structures that have selected physical and/or chemical properties. The physical and/or chemical properties may be engineered into the individual nanofibrillar structures as described above. Viable cells are deposited onto the multi-layered nanofibrillar assembly and the assembly is cultured under conditions that promote growth and/or differentiation of the deposited cells.

In another embodiment, multiple cell types are cultured on individual nanofibrillar structures under different culture conditions and then assembled, manually or mechanically, layer by layer under sterile conditions into a specific multi-layered nanofibrillar assembly. Nano- and/or micro-environments that promote cellular activity of particular cell types may be engineered within an individual nanofibrillar structure by varying and/or modifying selected physical and/or chemical properties of the nanofibrillar structure or within the assembly by selectively layering the individual nanofibrillar structures to obtain the desired nano- or micro-environment. The physical and/or chemical characteristics may be engineered as described above. The multi-layered nanofibrillar assembly is than cultured under conditions that promote cellular activity, including cell growth and/or differentiation.

In another embodiment, multiple cell types are cultured on individual nanofibrillar structures under different culture conditions. The physical and chemical properties of the individual nanofibrillar structures may be customized for a particular cell type. The substrate and/or spacers of the nanofibrillar structures are biodegradable and/or biodesolvable allowing for controlled release of bioactive molecules during culture. The bioactive molecules are selected to promote a desired cellular activity, including growth and/or differentiation. The individual nanofibrillar structures are then assembled, manually or mechanically, layer by layer under sterile conditions into a multi-layered nanofibrillar assembly. The multi-layered assembly may be layered to create nano- and/or micro-environments that promote a desired cellular activity, including growth and/or differentiation. Biodegradable and/or biodesolvable spacers comprising selected bioactive molecules may be inserted between the layered nanofibrillar structures comprising the assembly to fine tune nano- and/or micro-environments within the assembly. The rate of release of the bioactive molecules from the spacer may be determined by the rate of biodegradation and/or biodissolution of the polymer comprising the spacer. The assembled cellular array is than cultured under conditions that promote cellular activity, including cell proliferation and/or differentiation.

In another embodiment, nanofibrillar structures are individually wrapped and sterilized. After removal from the packaging, the nanofibrillar structures may be assembled manually or mechanically, layer by layer, within a culture container to form a multi-layered nanofibrillar assembly.

Degradation and potential redistribution within the body of new materials for in vivo applications, such as the nanofibrillar structure and multi-layered nanofibrillar assembly of the invention, need to be evaluated. Materials that are implanted into specific sites within the body can be degraded and then transported to other regions that are distant from the original site of incorporation. To examine the degradation properties of the nanofibers within the body, the nanofiber network, substrate, and/or spacers comprising the individual nanofibrillar structures the of the multi-layered assembly may be labeled with a fluorescent marker as described above for the improved nanofiber. In an embodiment, the fluorescent marker is a quantum dot. Because quantum dots are both fluorescent and opaque to magnetic resonance imaging, both multi-photon fluorescence microscopy (for examination of isolated tissues) and MRI (for in vivo analysis) may be used to detect and track the distribution of quantum dot containing fragments or decomposition products of the multi-layered nanofibrillar assembly within tissues and determine whether the decomposition products of the assembly elicit a significant foreign body response when incorporated into different tissues or sites within the a body.

iv. Additional Uses

In another application, the nanofibrillar structures of the invention may be used in high throughput applications for analyzing drug/cell interactions. High throughput applications are a valuable approach for discovery of new pharmaceuticals. High throughput applications utilize multiwell tissue culture chambers with densities up to about 1536 wells per plate. Increasing the population of cells per well would serve to increase the measured signals. In an embodiment, nanofibrillar structures may be inserted into a well. In another embodiment, a surface of the well may function as the substrate allowing the nanofiber network to be deposited directly onto a surface of the well. The introduction of such nanofibrillar structures into the wells provides additional surfaces for cell, ligand, and/or enzyme attachment without affecting the ability to perform optical measurements.

In another application, the nanofibrillar structure may be used in purification and/or separation applications. Individual nanofibrillar structures may be layered to form a chromatography column. Physical and/or chemical properties including size, charge, hydrophobicity, and affinity for other molecules may be exploited to separate, for example, a protein from a solution. In an embodiment, individual nanofibrillar structures may be layered to form an affinity column. Physical and/or chemical properties including, for example, specific functional groups, polypeptides comprising a specific receptor, or immunoglobulins, may be engineered into or attached to the nanofibrillar structures to selectively bind specific polypeptides from a solution. The solution is passed through the multi-layered nanofibrillar assembly allowing the polypeptides to bind to the matrix. The bound polypeptides may be released from the assembly with a solvent. In another embodiment, individual nanofibrillar structures may be layered to form a filtration column. Physical properties including, for example, porosity and fibril density may be engineered into the multi-layered nanofibrillar assembly to allow polypeptides to be separated from a solution according to their size. In another embodiment, individual nanofibrillar structures may be layered to form an ion-exchange column. Chemical properties including, for example, negatively and/or positively charged functional groups may be engineered into or attached to the nanofibrillar structures.

In another application, the structures of the invention may be used to fabricate a bioreactor.

C. Cell Growth Media

Another aspect of the invention is a cell growth media. The cell growth media may comprise a matrix, mat, network, sheet, or roll. In an embodiment, the media comprises a matrix of nanofibers. The nanofibers may be fabricated from a polymer or polymer system as described above for the improved nanofiber. The cell growth media may be deposited on the surface of a culture container or into a culture container.

The growth media may be fabricated to desired dimensions for use in a culture container. In an embodiment, the cell growth media comprises a matrix of nanofibers wherein the network has a fiber diameter of about 50 nm to about 1000 nm, an average interfiber spacing of at least about 2 microns, a matrix solidity of about 30 percent or less, and a top and a bottom with an outerwall wherein the outerwall has a height of about 10 microns to about 100 mm and wherein the top and bottom independently have an area of about 5 mm$^2$ to about $4\times10^5$ mm$^2$. The growth media may be sized or resized to selected dimensions for use in a culture container by cutting down to size a sheet, roll, matrix, network, or mat comprising the growth media or cutting a piece with the desired dimensions from a matrix, sheet, roll, network, or mat comprising the growth media. In another embodiment, the cell growth media comprises a network of nanofibers wherein the dimensions of the network are adapted for insertion into a culture container.

The cell growth media may be used in a variety of applications, including cell culture and tissue culture applications. Any cell described above may be grown on the cell growth media. In an embodiment, cell growth media is individually wrapped and sterilized. After removal from the packaging, the media may be placed within a culture container to form a surface for cell growth. In another embodiment, cell growth media is deposited onto an inside surface of a culture container. The culture containers comprising the cell growth matrix may be individually wrapped and sterilized. After removal from the packaging, cells may be deposited onto the cell growth media within the culture container. Cells grown in the cell growth media have many in vivo and ex vivo uses including wound repair, growth of artificial skin, veins, arteries, tendons, ligaments, cartilage, heart valves, organ culture, treatment of burns, and bone grafts.

The physical properties and/or characteristics of the cell growth media including, but not limited to, texture, rugosity, adhesivity, porosity, elasticity, solidity, geometry, and fibril density may be varied and/or modified to promote a desired cellular activity, including growth and/or differentiation. Specific nano- and/or micro-environments may be engineered within the cell growth media. For example, the porosity and fibril density of the cell growth media may be varied and/or modified to allow a cell to penetrate the cell growth media and grow in a three dimensional environment. The physical properties of the cell growth media may be engineered as described above for the improved nanofiber and/or nanofibrillar structure.

Specific recognition motifs such as peptides, lipids, carbohydrates, amino acids, nucleotides, nucleic acids, polynucleotides, or polysaccharides including but not limited to growth factors, differentiation factors, fibrous proteins, adhesive proteins, glycoproteins, functional groups, adhesive compounds, deadhesive compounds, and targeting molecules may be engineered into the cell growth media either isotropically or as gradients to promote desired cellular activity, including cell growth and/or differentiation. The chemical properties of the cell growth media may be engineered as described above for the improved nanofiber and/or nanofibrillar structure.

In another application, the cell growth media of the invention may be used in high throughput applications for analyzing drug/cell interactions. High throughput applications utilize multiwell tissue culture chambers with densities up to about 1536 wells per plate. Increasing the population of cells per well would serve to increase the measured signals. In an embodiment, cell growth media may be inserted into the wells of the tissue culture chamber used for the analysis. In another embodiment, a surface of the well may function as a substrate for the cell growth media allowing a nanofiber network or matrix to be deposited directly onto a surface of the well. The introduction of such cell growth into the wells provides additional surfaces for cell, ligand, and/or enzyme attachment without affecting the ability to perform optical measurements.

EXAMPLES

The invention is illustrated by the following Examples, which serve to exemplify the embodiments. Many variations and embodiments, however, can be made to the disclosed invention. The Examples are not intended to limit the invention in any way.

Example 1

Electrospinning a Polymer Solution Comprising a Lipid Produces an Enhanced Population of Thin Fibers To visualize the changes in fiber diameter associated with the addition of a lipid to a polymer solution using an optical microscope, fibers were electrospun to obtain microfibers. Microfibers were electrospun from a solution comprising 15% poly($\epsilon$-caprolactone) (w/w) in chloroform supplemented with (Dow Tone Polymers, Midland, Mich.) 0, 0.25, 0.5, 1.0 and 1-% respectively of cholesterol (w/w) (Sigma, St. Louis, Mo.). The fibers were electrospun using a capillary needle system. An Eppendorf micropipette tip (yellow) was fitted to a 5 cc syringe. The polymer solution was poured into the syringe and a positive electrode connected to a Nanosecond Optical Pulse Radiator Model NR-1 (Optitron, Inc., Torrance, Calif.) was inserted into the solution. The electrospinning voltage was 18,000 volts. The fibers were electrospun onto a grounded metal plate target spinning in a plane perpendicular to the syringe. The target was placed 2 inches from the tip of the micropipetter. The fibers were collected on overhead transparency placed on the target. The fibers were viewed on a light microscope (Insight Bilateral Scanning Confocal Fluorescence Microscope (Meridian Instruments, Okemos, Mich.) with a 20× objective and the images were digitally acquired with a CCD camera.

Figure 2:
FIGS. 2A-E are photomicrographs showing a comparison of microfibers electrospun from polymer solutions comprising increasing amounts of a lipid.
Figure 2:
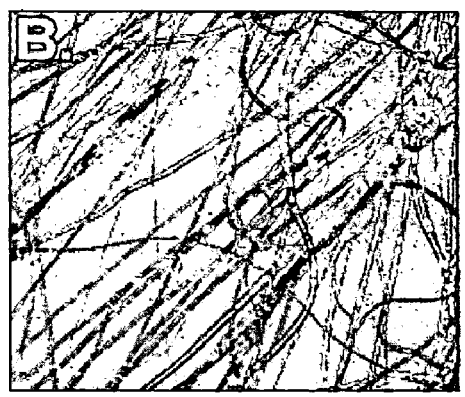
Figure 2:
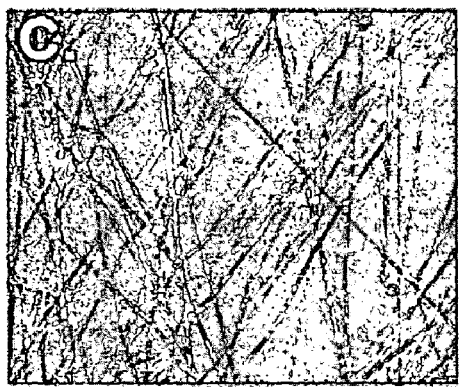
Figure 2:
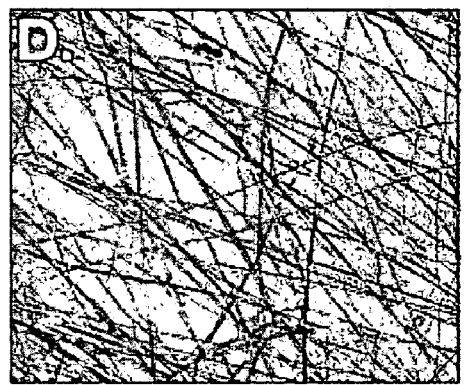
Figure 2:

As shown in FIGS. 2A-E, addition of cholesterol to the polymer solution produces fibers with progressively smaller diameters. Increasing the amount of cholesterol added to the polymer solution produced fibers with progressively smaller diameters. Fibers produced from a polymer solution comprising no cholesterol had a range of diameters from of 10-50 microns. (FIG. 2A). Fibers produced from a polymer solution comprising 0.25% cholesterol (w/w) had a range of diameters from 5-30 microns. (FIG. 2B). Fibers produced from a polymer solution comprising 0.5% cholesterol (w/w) had a range of diameters from 2-20 microns. (FIG. 2C). Fibers produced from a polymer solution comprising 1.0% cholesterol (w/w) had a range of diameters from 1-15 microns. (FIG. 1D). Fibers produced from a polymer solution comprising 10% cholesterol (w/w) had a diameter of 0.8-8 microns. (FIG. 2E).

Example 2

Nanofibers Comprising a Lipid Induce Tight Attachment of Cells to the Nanofiber

Nanofibers comprising a lipid provide a surface that promotes recruitment of cells and tight association between the cells and nanofibers. Normal kidney rat (NRK) fibroblasts were cultured on nanofibers electrospun from a solution comprising 10% poly($\epsilon$-caprolactone) (w/w) in chloroform supplemented with 0.25% sphingomyelin in Dulbecco Modified Eagle's Medium (DME) at 37° C. in 5% $CO_2$ and visualized on a light microscope (Insight Bilateral Scanning Confocal Fluorescence Microscope (Meridian Instruments, Okemos, Mich.)) with a 20× objective. Images were captured with a CCD camera.

Figure 3:
FIGS. 3A and B are photomicrographs showing a comparison of normal rat kidney fibroblasts grown on tissue culture plates coated with nanofibers comprising a lipid or nanofibers not comprising a lipid.
Figure 3:

As shown in FIGS. 3A and B, nanofibers comprising 0.25% sphingomyelin induce a rapid recruitment of cells and their attachment to the nanofibers. FIG. 3A shows NRK fibroblasts after two days of culture on a tissue culture plate coated with nanofibers comprising 0.25% sphingomyelin. The fibroblasts are tightly attached to the nanofibers and have spread and divided to fill the spaces between the fibers forming a monolayer. FIG. 3B shows NRK fibroblasts after two days of culture on a tissue culture plate coated with nanofibers not containing sphingomyelin. Few cells are attached to the nanofibers. The guided migration and tight attachment properties of the lipo-containing nanofibers suggest the fibers may be useful in vivo or ex vivo for applications including wound repair, growth of artificial skin, veins, arteries, tendons, ligaments, cartilage, heart valves, organ culture, treatment of burns, and bone grafts

Example 3

Cells Grown on Nanofiber Network have Actin Networks Similar to Cells within Tissue The actin network of a cell has been utilized as a marker to determine which cell culture methods most closely approximate the environments within tissues (Cukierman et al., 2001, *Science*, 23:1708-1712; Walpita and Hay, 2002, *Nature Rev. Mol. Cell. Biol.*, 3:137-141). When grown in two-dimensional tissue culture, fibroblasts assume a highly spread and adhering morphology in which the actin network located within the cytoplasm is organized into arrays of thick stress fibers. In contrast, fibroblasts observed in tissues are spindle-like in shape with actin organized in a cortical ring (Walpita and Hay, 2002, *Nature Rev. Mol. Cell. Biol.*, 3:137-141).

We compared the actin network of normal rat kidney (NRK) fibroblasts grown on two-dimensional and three-dimensional surfaces. Fibroblasts were grown on polyamide nanofiber network, glass, and glass coated with polylysine. The polyamide nanofibers were spun using either a rotating emitter system or a capillary needle system. Both systems produce substantially the same fibrous materials. The flow rate was 1.5 mil/min per emitter, a target distance of 8 inches, an emitter voltage of 88 kV, a relative humidity of 45%, and for the rotating emitter an rpm of 35.

Formation of actin networks was monitored by imaging the distribution of green fluorescent protein (GFP)-actin chimera expressed by the NRK fibroblasts. Briefly, NRK fibroblasts transfected with GFP-actin (gift from Dr. Sanford Simon, Laboratory of Cellular Biophysics, Rockefeller University, New York, N.Y.) were cultured on polyamide nanofibers, glass, or glass coated with poly 1-lysine in Dulbecco Modified Eagle's Medium (DME) at 37° C. in 5% $CO_2$ and than examined using an Insight Bilateral Scanning Confocal Fluorescence Microscope (Meridian Instruments, Okemos, Mich.).

Figure 4:
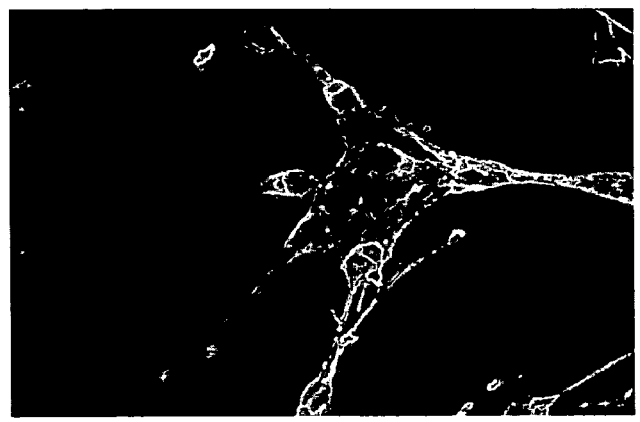
FIGS. 4A-C are photomicrographs showing a comparison of normal rat kidney fibroblasts grown on polyamide nanofiber network, glass, and glass coated with polylysine.
Figure 4:
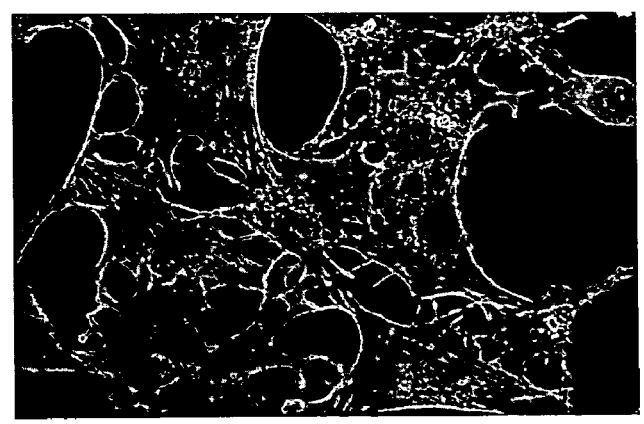
Figure 4:
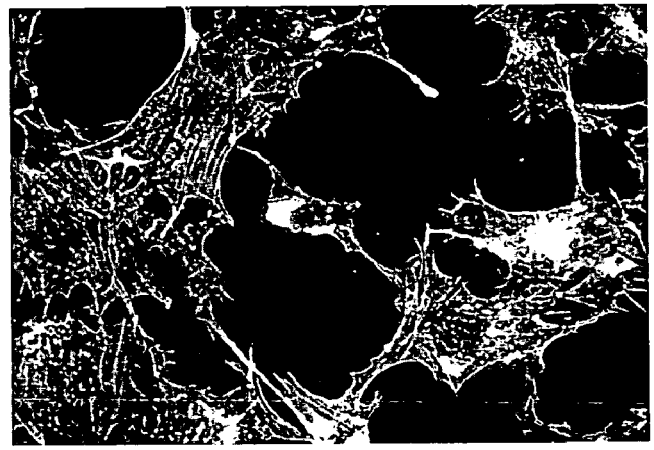

As shown in FIGS. 4A-C, cells grown on the three-dimensional growth environment of the nanofiber network organize cytoskeletal networks similar to those observed in vivo. Fibroblasts grown on a nanofiber network demonstrated a more spindle like morphology with filipodia and demonstrated few stress fibers. (FIG. 4A) In contrast, fibroblasts grown on a glass surface were spread with many stress fibers. (FIG. 4B). Fibroblasts grown on a poly 1-lysine coated glass surface were more spread and showed thicker and more pronounced stress fibers (FIG. 4C).

These micrographs also demonstrate that confocal microscopy offers a rapid means to monitor differences in the organization of cytoskeletal networks in live cells or tissues as a function of various fiber manipulations including physical properties of the fiber network including, but not limited to, texture, rugosity, adhesivity, porosity, elasticity, geometry, and fibril density, and chemical properties of the fiber network including, but not limited to, growth factors, differentiation factors, fibrous proteins, adhesive proteins, glycoproteins, functional groups, adhesive compounds, deadhesive compounds, and targeting molecules. Comparison of cytoskeletal networks of cells or tissues cultured on a nanofiber network with in vivo observations allows fine-tuning of physical and/or chemical properties of the nanofiber network to more closely mimic the in vivo environment of a cell or tissue.

Example 4

Incorporation of Functional Groups into Nanofibers

Figure 5:
FIGS. 5A and B are photomicrographs showing that incorporation of amino functional groups onto the surface of nanofibers.
Figure 5:

Functional groups such as alcohol, aldehyde, amino, carboxy, and sulphydryl functional groups and photoactivatable functional groups, such as carbene or nitrene may be incorporated onto the surface of nanofibers. These groups may be used to covalently couple bioactive molecules including, but not limited to, polypeptides such as growth factors or differentiation factors, carbohydrates, lipids, polysaccharides, or therapeutic drugs. Functional groups may be incorporated into a nanofiber by adding the functional groups into the polymer solution. Nanofibers were electrospun from a solution comprising 10% poly(ε-caprolactone) (w/w) in chloroform supplemented with (Dow Tone Polymers, Midland, Mich.) 2% dodecyl amine (w/w) (Sigma, St. Louis, Mo.) as described for Example 1. To demonstrate the availability of modifiable amines at the surface of the nanofibers, the nanofibers were reacted with fluorescein isothiocyanate (1 mg/ml stock solution in water) (Sigma, St. Louis, Mo.) in 2.0% sodium phosphate buffer, pH 8.5. Incorporation of fluorescence into the fibers was shown utilizing an Insight Bilateral Scanning Confocal Fluorescence Microscope (Meridian Instruments, Okemos, Mich.). As shown in FIG. 5A, a low level of fluorescence was observed on the surface of unmodified fibers that is a result of unreacted fluorescein isothiocyanate adsorbed onto the fiber surface. In contrast, on nanofibers containing incorporated amino groups, significant fluorescence was observed along the entire fiber following reaction with fluorescein isothiocyanate (FIG. 5B).

This data demonstrates that the modified surfaces of the nanofibers contain functional groups that are available for coupling with bioactive molecules allowing for customized incorporation of molecules such as growth factors, differentiation factors, fibrous proteins, adhesive proteins, glycoproteins, functional groups, adhesive compounds, deadhesive compounds, and targeting molecules to create a nano- and/or micro-environment within the nanofiber network that promotes one or more selected activities in a cell or tissue, including growth and/or differentiation. This data also suggests that nanofibers comprising different functional groups in specific spatial and geometric arrangements may be induced to self-assemble into a geometrically defined array of peptide derivatized fibers by introducing peptides having the appropriate reactive groups.

Example 5

Labeling Fine Fibers with Quantum Dots

Figure 6:
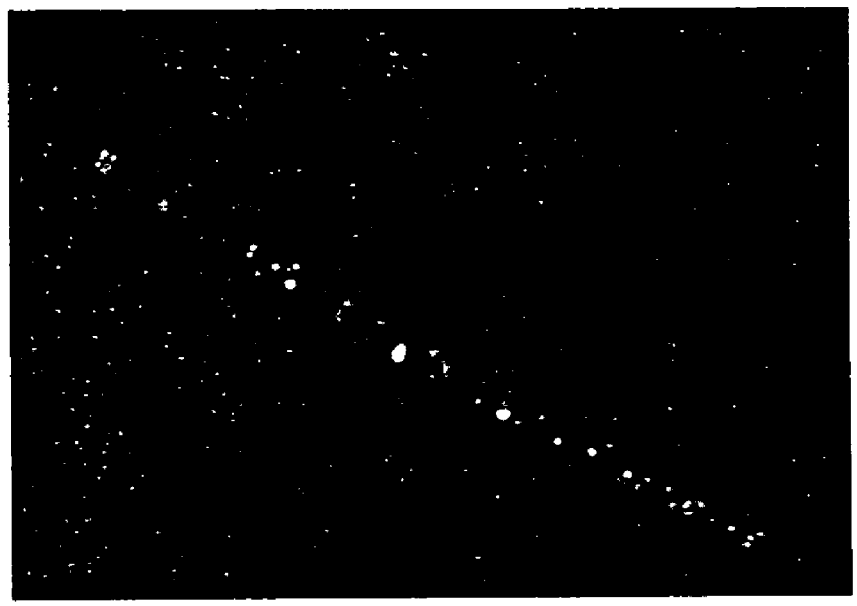
FIG. 6 is a photomicrograph showing the fluorescent labeling of nanofibers with quantum dots.

In order to prepare fibers with different chemical and/or physical properties and incorporate them into nanofiber blends or specific cellular arrays while still maintaining the ability to identify each type of fiber within the blend or cellular array, we studied incorporating fluorescent labels into the nanofiber. A 1% solution of quantum dots (gift of Dr. Sanford Simon, Laboratory of Cellular Biophysics, Rockefeller University, New York, N.Y.) was added to a polymer solution comprising 12% poly(ε-caprolactone) (w/w) in chloroform. The solution was then electrospun as described for Example 1 producing a population of microfibers containing quantum dots. The fibers were excited at 488 nm and images of the quantum dot distribution within the microfibers were collected using an Insight Bilateral Scanning Confocal Fluorescence Microscope (Meridian Instruments, Okemos, Mich.) (FIG. 6).

Fluorescence of quantum dots is quenched in aqueous environments. Addition of water to the microfibers did not quench the fluorescence of the quantum dots, demonstrating that the quantum dots were embedded within the fiber matrix rather than absorbed to the surface of the fiber, an important consideration for their use in aqueous systems.

The above specification, examples and data provide an explanation of the invention. However, many variations and embodiments can be made to the disclosed invention. The invention is embodied in the claims herein after appended.

We claim:

1. A nanofibrillar structure for the proliferation and/or differentiation of cells in cell culture comprising one or more synthetic polymeric nanofibers and a non-cytotoxic substrate, wherein the nanofibrillar structure is defined by a network of one or more nanofibers, the network having a thickness of a single nanofiber to about 2000 nanometers, wherein the nanofibrillar structure is deposited on a surface of the substrate and comprises one or more nanofibers having a diameter of about 50 to about 1000 nanometers, an average interfiber spacing of about 0.01 microns to about 25 microns, and a solidity of 30 percent to 70 percent; and wherein the nanofibrillar structure promotes the proliferation and/or differentiation of cells cultured on said nanofibrillar structure.

2. The nanofibrillar structure of claim 1, wherein the nanofibrillar structure comprises a solidity of 30 percent to 50 percent.

3. The nanofibrillar structure of claim 1, wherein the substrate is a porous plastic substrate.

4. The nanofibrillar structure of claim 1, comprising an average interfiber spacing of 2 microns.

5. The nanofibrillar structure of claim 1, wherein the nanofibrillar structure is substantially free of collagen.

6. The nanofibrillar structure of claim 1, wherein the network of one of more nanofibers has a thickness of about 100 nanometers to about 1000 nanometers.

7. The nanofibrillar structure of claim 1, wherein the substrate is a film.

8. The nanofibrillar structure of claim 7, wherein the one or more nanofibers has diameter of about 50 to 1000 nanometers, an average interfiber spacing of at least about 2 microns and a solidity of 30 percent to 70 percent.

9. The nanofibrillar structure of claim 8, wherein the nanofibrillar structure comprises a solidity of 30 percent to 50 percent.

10. The nanofibrillar structure of claim 8, wherein the film is water soluble.

11. The nanofibrillar structure of claim 8, wherein the film is water insoluble.

12. The nanofibrillar structure of claim 10, wherein the film is a polyvinyl alcohol film.

13. The nanofibrillar structure of claim 8, wherein the film is biodegradable.

14. The nanofibrillar structure of claim 8, wherein the film is biocompatible.

15. The nanofibrillar structure of claim 1, wherein the substrate is a non-porous glass substrate.

16. The nanofibrillar structure of claim 8, wherein the film is porous.

17. The nanofibrillar structure of claim 8, wherein the structure comprises one or more growth factors.

18. The nanofibrillar structure of claim 17, wherein at least one of the growth factors is vascular endothelial growth factor, bone morphogenic factor β, epidermal growth factor, endothelial growth factor, platelet-derived growth factor, neural growth factor, fibroblast growth factor, insulin growth factor, or transforming growth factor.

19. The nanofibrillar structure of claim 17, wherein the structure releases the growth factors.

20. The nanofibrillar structure of claim 19, wherein the rate of release is determined by the rate of dissolution or degradation of the film or the one or more nanofibers.

21. The nanofibrillar structure of claim 8, wherein the structure comprises one or more differentiation factors.

22. The nanofibrillar structure of claim 21, wherein at least one of the differentiation factors is neurotrophin, colony stimulating factor, or transforming growth factor.

23. The nanofibrillar structure of claim 21, wherein the film or one or more nanofibers releases the differentiation factors.

24. The nanofibrillar structure of claim 23, wherein the rate of release is determined by the rate of dissolution or degradation of the film or the one or more nanofibers.

25. The nanofibrillar structure of claim 1, wherein the one or more nanofibers is made of a non-cytotoxic polymer.

26. The nanofibrillar structure of claim 25, wherein the polymer is biodegradable.

27. The nanofibrillar structure of claim 25, wherein the polymer is water soluble.

28. The nanofibrillar structure of claim 25, wherein the polymer is water insoluble.

29. The nanofibrillar structure of claim 25, wherein the polymer is polyester.

30. The nanofibrillar structure of claim 29, wherein the polyester is poly epsilon caprolactone, polyglycolate, or polylactate.

31. The nanofibrillar structure of claim 25, wherein the polymer is polyamide.

32. The nanofibrillar structure of claim 31, wherein the polyamide is a nylon.

33. The nanofibrillar structure of claim 25, wherein the one or more nanofibers further comprises one or more bioactive molecules.

34. The nanofibrillar structure of claim 33, wherein at least one of the bioactive molecules is a lipid, carbohydrate, polysaccharide, amino acid, nucleotide, nucleic acid, polynucleotide or hybrid molecule thereof.

35. The nanofibrillar structure of claim 34, wherein the lipid is lysophosphatidylcholine, phosphatidylcholine, sphingomyelin, cholesterol, or mixtures thereof.

36. The nanofibrillar structure of claim 34, wherein the polysaccharide is cellulose, starch, alginic acid, chitosan, or hyaluronan.

37. The nanofibrillar structure of claim 25, wherein the one or more nanofibers further comprises a biological compound that promotes attachment of a cell to the nanofiber.

38. The nanofibrillar structure of claim 25, wherein the one or more nanofibers further comprises one or more alcohol, aldehyde, amine, carboxy, sulphydryl, or photoactivatable functional groups.

39. The nanofibrillar structure of claim 38, wherein the photoactivatable group is carbene or nitrene.

40. A nanofibrillar structure of claim 1, wherein the one or more nanofibers comprises one or more growth factors.

41. The nanofibrillar structure of claim 40, wherein at least one of the growth factors is vascular endothelial growth factor, bone morphogenic factor β, epidermal growth factor, endothelial growth factor, platelet-derived growth factor, neural growth factor, fibroblast growth factor, insulin growth factor, or transforming growth factor.

42. The nanofibrillar structure of claim 40, wherein the one or more nanofibers releases one or more growth factors.

43. The nanofibrillar structure of claim 42, wherein the rate of release of the growth factors is determined by the rate of degradation or dissolution of the nanofibrillar structure.

44. The nanofibrillar structure of claim 1, wherein the one or more nanofibers comprises one or more differentiation factors.

45. The nanofibrillar structure of claim 44, wherein at least one of the differentiation factors is neurotrophin, colony stimulating factor, or transforming growth factor.

46. The nanofibrillar structure of claim 44, wherein the one or more nanofibers releases one or more differentiation factors.

47. The nanofibrillar structure of claim 44, wherein the rate of release of the differentiation factors is determined by the rate of degradation or dissolution of the nanofibrillar structure.

48. The nanofibrillar structure of claim 1 comprising a width and depth sufficient for insertion into a culture container.

49. The nanofibrillar structure of claim 48, wherein the width and depth of the nanofibrillar structure is sufficient for insertion into a well in a culture plate.

50. The nanofibrillar structure of claim 48, wherein the culture container is selected from the group consisting of single well culture plates, multiwell culture plates, chambered culture slides, multi-chambered culture slides, coverslips, cups, flasks, tubes, bottles, perfusion chambers, bioreactors and fermentors.

51. A tissue culture container comprising the nanofibrillar structure of claim 1.

52. A tissue culture container of claim 51, wherein the culture container is selected from the group consisting of single well culture plates, multiwell culture plates, chambered culture slides, multi-chambered culture slides, coverslips, cups, flasks, tubes, bottles, perfusion chambers, fermentors, and bioreactors.

53. The nanofibrillar structure of claim 1, wherein the nanofibrillar structure is substantially free of collagen, fibrin, fibrinogen, thrombin, or mixtures thereof.

54. A method of producing the nanofibrillar structure of claim 1, comprising electrospinning a network of one or more nanofibers.

55. A method of producing the nanofibrillar structure of claim 1, comprising electrospinning a network of one or more nanofibers onto a surface of the substrate.

56. A multi-layered nanofibrillar assembly, comprising two or more nanofibrillar structures according to claim 1 layered to form a multi-layered assembly.

57. The multi-layered nanofibrillar assembly of claim 56, further comprising a spacer having a thickness and a first and second surface wherein the first surface of the spacer contacts a surface of a first nanofibrillar structure and a second surface of the spacer contacts a surface of a second nanofibrillar structure such that the first and second nanofibrillar structures are separated by the thickness of the spacer.

58. The multi-layered nanofibrillar assembly of claim 56, comprising an average interfiber spacing of 2 microns.

59. The multi-layered nanofibrillar assembly of claim 57, wherein the nanofibrillar structure is substantially free of collagen, fibrin, fibrinogen, thrombin, or mixtures thereof.

60. The multi-layered nanofibrillar assembly of claim 56, wherein the network of one of more nanofibers has a thickness of about 100 nanometers to about 1000 nanometers.

* * * * *